United States Patent
Pedersen et al.

(10) Patent No.: US 10,615,766 B2
(45) Date of Patent: Apr. 7, 2020

(54) AUDIO PROCESSING DEVICE, SYSTEM, AND METHOD IN WHICH FREQUENCY BANDS OF AN INPUT AUDIO SIGNAL ARE BUNDLED AND ALLOCATED TO CHANNELS FOR PROCESSING

(71) Applicant: Oticon A/S, Smørum (DK)

(72) Inventors: Michael Syskind Pedersen, Smørum (DK); Gary Jones, Smørum (DK); Søren Kamaric Riis, Smørum (DK); Karsten Bo Rasmussen, Smørum (DK); Julian Skovgaard, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 16/217,964

(22) Filed: Dec. 12, 2018

(65) Prior Publication Data

US 2019/0181823 A1    Jun. 13, 2019

(30) Foreign Application Priority Data

Dec. 13, 2017 (EP) .................................... 17206989

(51) Int. Cl.
*H04R 25/00* (2006.01)
*H03G 9/02* (2006.01)
(Continued)

(52) U.S. Cl.
CPC ........... *H03G 9/025* (2013.01); *H04R 25/353* (2013.01); *H04R 25/356* (2013.01);
(Continued)

(58) Field of Classification Search
None
See application file for complete search history.

(56) References Cited

U.S. PATENT DOCUMENTS

| 9,351,086 B2 | 5/2016 | Petersen et al. |
| 2010/0239100 A1 | 9/2010 | Steinbuss |

(Continued)

FOREIGN PATENT DOCUMENTS

| EP | 3 122 072 A1 | 1/2017 |
| WO | WO 98/47313 A2 | 10/1998 |
| WO | WO 98/47313 A3 | 2/1999 |

*Primary Examiner* — James K Mooney
(74) *Attorney, Agent, or Firm* — Birch, Stewart, Kolasch & Birch, LLP

(57) ABSTRACT

The invention relates to a hearing aid comprising a first microphone configured to receive a first acoustic signal and to convert the first acoustic signal to a first electrical audio signal, a speaker configured to emit an acoustic output signal into an ear of a user of the hearing aid device, a first analog-to-digital converter for converting the first electrical audio signal into a first time-domain input signal, a first input unit comprising a first analysis filter bank which is configured to convert the first time-domain input signal to a number NI,1 of first input frequency bands wherein the number NI,1 of first input frequency bands is determined by said first analysis filter bank, a first frequency band bundling and allocation unit which is configured to bundle adjacent first input frequency bands and to allocate first frequency bands to be processed to a number NP,1 of first processing channels, a memory unit which is configured to store data indicating which of the first NI,1 input frequency bands are subject to a likelihood of feedback that is above a threshold, a signal processing unit is configured to process the first frequency bands to be processed in the number NP,1 of first processing channels, and wherein the number NP,1 of first processing channels is smaller than the number NI,1 of first input frequency bands, and wherein the first frequency band bundling and allocation unit is configured to generate a first bundling and allocation scheme which determines the bundling of the first NI,1 input frequency bands and the allo- (Continued)

cation of the first frequency bands to be processed to the first $N_{P,1}$ processing channels wherein said first bundling and allocation scheme depends on the likelihood of feedback to occur in at least one of the first $N_{I,1}$ input frequency bands.

20 Claims, 9 Drawing Sheets

(51) Int. Cl.
*H04R 27/00* (2006.01)
*H04R 1/10* (2006.01)

(52) U.S. Cl.
CPC ......... *H04R 25/407* (2013.01); *H04R 25/453* (2013.01); *H04R 1/1016* (2013.01); *H04R 25/405* (2013.01); *H04R 25/552* (2013.01); *H04R 25/554* (2013.01); *H04R 27/00* (2013.01); *H04R 2225/43* (2013.01); *H04R 2227/007* (2013.01); *H04R 2227/009* (2013.01); *H04R 2430/03* (2013.01); *H04R 2460/03* (2013.01)

(56) References Cited

U.S. PATENT DOCUMENTS

| | | |
|---|---|---|
| 2012/0177205 A1 | 7/2012 | Bramsløw et al. |
| 2013/0170660 A1 | 7/2013 | Kristensen et al. |
| 2014/0348360 A1 | 11/2014 | Gran |
| 2016/0165361 A1 | 6/2016 | Miller et al. |

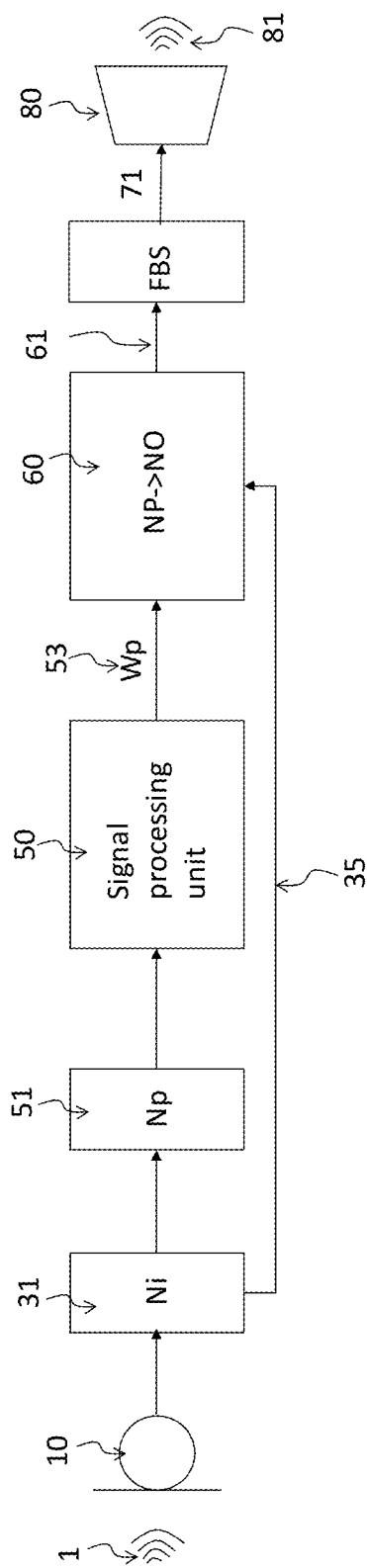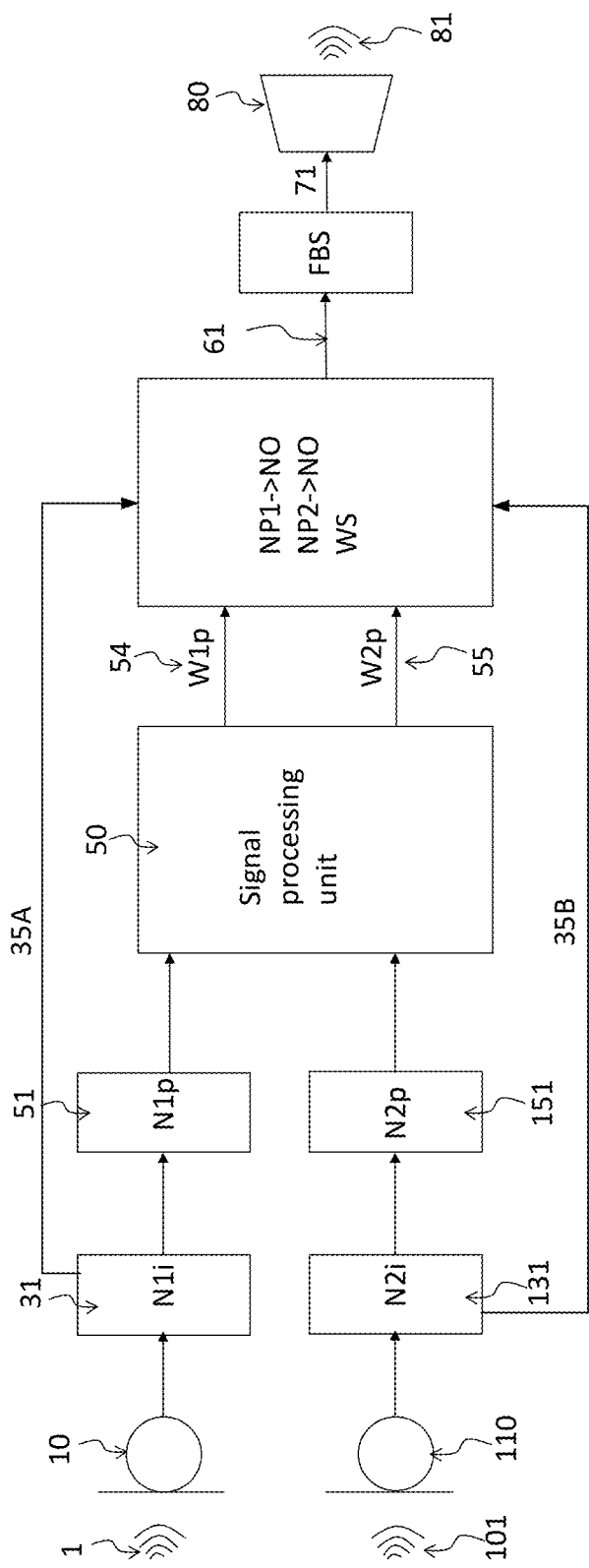
Fig. 2
Fig. 3

AUDIO PROCESSING DEVICE, SYSTEM, AND METHOD IN WHICH FREQUENCY BANDS OF AN INPUT AUDIO SIGNAL ARE BUNDLED AND ALLOCATED TO CHANNELS FOR PROCESSING

TECHNICAL FIELD

The invention relates to a hearing aid device that is configured to implement a frequency band bundling scheme and a method of processing an input audio signal.

BACKGROUND

A digital hearing aid device typically comprises an input transducer such as a micro-phone to receive sound from an ambient environment and convert the received acoustic signal to an electrical audio signal. The electrical audio input signal is a signal in the frequency domain and is converted to a time-domain input signal using an analog-to-digital converter. Further, the time-domain input signal is converted to a number of input frequency bands. Typically, the number of input frequency bands is determined by an analysis filter bank which also includes filter coefficients to provide gain to selected frequency bands, e.g. according to a specific hearing situation. In a processing unit the number of frequency bands is processed in a number of processing channels. The processing of the number of frequency bands requires sufficient computational power and consequently energy provided e.g. by a battery. Eventually, the processed frequency bands are converted via a digital-to-analog converter into an electric audio output signal that in turn is converted into audible sound and emitted as an acoustic output signal into an ear of a user using a (loud-)speaker, also called a receiver. The speaker can be located in the ear canal of the user. Based on a hearing aid device as described above the hearing experience of a user can be improved.

Typically, a digital hearing aid device can be programmed by connecting it to an external computer. This allows additional processing features to be implemented. Thereby, the processing characteristics can be adjusted enabling e.g. an amplification or suppression of selected frequency bands. Sometimes processing characteristics can be adjusted by a user itself according to different hearing situations. Even programs that adjust the processing characteristics automatically and adaptively can be implemented. Based on such programs e.g. acoustic feedback or background noise can be adaptively reduced or the processing of the received sound signal can be automatically adapted to different hearing situations. Consequently, a user's comfort can be increased.

In order to decrease the computational effort and, thus, to save energy, it can be advantageous to bundle input frequency bands and to allocate a smaller number of frequency bands to be processed to processing channels of a signal processing unit. After processing the smaller number of frequency bands, the processed frequency bands can be redistributed to a larger number of output frequency bands such that the resolution of frequency bands is increased again.

EP 3122072 A1 describes an audio processing device comprising an input unit for converting a time-domain input signal to a number of input frequency bands and an output unit for converting a number of output frequency bands to a time-domain output signal. The object of the described audio processing device is to provide a flexible audio processing scheme, e.g. adapted to characteristics of the input signal. This allows that the audio processing can be adapted to a particular acoustic environment and/or to a user's needs (e.g. hearing impairment) with a view to minimizing power consumption and/or processing frequency resolution.

Hearing aid devices can be implemented e.g. as behind-the-ear (BTE) hearing aids which typically have the microphone arranged behind the ear canal of a user or as in-the-ear (ITE) hearing aids which typically have the microphone arranged in the ear of a user. In both cases a speaker is typically placed inside a user's ear canal in order to stimulate the eardrum. An advantage of a BTE hearing aid is that the distance between microphone and speaker, also known as feedback path, is larger compared to an ITE hearing aid such that the BTE hearing aid is less affected by feedback. As a consequence, in BTE hearing aids a higher gain can be applied to individual frequency bands without resulting in feedback.

In case a hearing aid device, e.g. a BTE or an ITE hearing aid, comprises a directional microphone with two microphones or two sound inlets, the directional system can be configured such that the directional pattern aims at cancelling the feedback path. This means that the directional response has its minimum directivity towards the feedback path. The directional pattern represents the directionality of the directional system.

In U.S. Pat. No. 9,351,086 B2 an ITE hearing aid is described which inter alia comprises a directional microphone and a feedback suppression system for counteracting acoustic feedback on the basis of sound signals detected by the two microphones or the two sound inlets. The described hearing aid device comprises an "open fitting" providing ventilation. The two microphones or the two sound inlets of the directional microphone (forming part of a directional system) are arranged in the ear canal at the same side of the receiver and sound is allowed to propagate freely between the microphones or between the inlets of the directional microphone and the receiver. It is preferred that the hearing aid device comprises a procedure (such as an adaptive procedure) for optimizing the directional system of the hearing aid device. Thereby, an improved feedback reduction is achieved, while allowing a relatively large gain to be applied to the incoming signal.

SUMMARY

It is an object of the invention to provide an improved hearing aid device.

According to the invention, the object is achieved by a hearing aid device comprising a first input transducer configured to receive a first acoustic signal and to convert the first acoustic signal to a first electrical audio signal. The input transducer can be a microphone or any other kind of input transducer. A microphone can be a microphone integrated in the hearing aid device and/or a remote microphone that operates wirelessly or it can be a wire-bound microphone.

A first analog-to-digital converter converts the first electrical audio signal into a first time-domain input signal and a first input unit (comprising a first analysis filter bank) is configured to convert the first time-domain input signal to a number $N_{I,1}$ of first input frequency bands. The number $N_{I,1}$ of first input frequency bands is determined by an analysis filter bank (e.g. the first analysis filter bank). The analysis filter bank can include filter coefficients which are configured to apply gain to selected frequency bands. Apparently, in case a frequency band has an increased likelihood of feedback to occur less gain is desirable.

The analysis filter bank could for example be a linear phase filter bank designed to allow distortion free combination (e.g. summation) of frequency band signals to frequency channel signals.

A first frequency band bundling and allocation unit can be configured to bundle adjacent first input frequency bands and to allocate first frequency bands to be processed to a number $N_{P,1}$ of first processing channels. The bundling can occur according to a bundling scheme that can be a matrix which includes the information if an input frequency band shall be bundled or not.

The advantage of bundling different frequency channels is mainly to save computational power as some computations are valid for a broader range of frequencies. Depending on the application different bundling schemes will be optimal.

The frequency band bundling and allocation is configured to perform the bundling of input frequency bands dynamically or statically. Also a mixture of static and dynamic bundling can be implemented. In case the frequency band bundling and allocation unit is configured to perform the bundling of input frequency bands dynamically, the bundling can occur during use of the hearing aid device. The bundling can then be adapted to different hearing situations during hearing device operation. In case of a static bundling of input frequency bands the frequency band bundling and allocation unit can be programmed such that the bundling scheme leads to predefined processing characteristics. A static frequency bundling scheme can be implemented e.g. by a hearing care professional before hearing aid device operation.

A memory unit is configured to store data indicating which of the first $N_{I,1}$ input frequency bands are subject to a likelihood of feedback that is above a (e.g. predefined) threshold. If the likelihood of feedback to occur in at least one of the input frequency bands is stored in the memory unit, the frequency bundling and allocation unit can be configured to determine the scheme based on the likelihood stored in the memory unit.

The likelihood of feedback to occur in at least one of the $N_{I,1}$ input frequency bands can be determined based on a feedback detection unit. The feedback detection unit can be comprised in the hearing aid device. Alternatively, the feedback detection unit can be comprised in an external device connected e.g. wirelessly to the hearing aid device. The likelihood of feedback to occur (e.g. to exceed a threshold value) in a particular frequency band can be determined in a variety of ways described in the prior art (e.g. based on correlation measures, e.g. cross-correlation between input and output signals of the hearing aid). The likelihood of feedback to occur in a particular frequency band can e.g. be adaptively determined (during use of the hearing aid). Alternatively of additionally, the likelihood of feedback to occur in at least one of the $N_{I,1}$ input frequency bands can be determined in a procedure in advance of use of the hearing aid by a user (e.g. during fitting of the hearing aid to a particular user).

Accordingly, if the hearing aid device comprises the feedback detection unit, the hearing aid device can be further configured to continuously determine the likelihood of feedback to occur in at least one of the input frequency bands. Thereby, the content of the bundling and allocation scheme will be updated continuously. The process of updating the bundling and allocation scheme in the dynamic case occurs according to the continuously determined likelihood of feedback.

In case, the likelihood of feedback to occur in at least one of the input frequency bands can be determined dynamically, the feedback detection unit can be further comprised in the hearing aid device. The frequency band bundling and allocation unit then adjusts the bundling scheme dynamically based on the by the feedback detection unit determined likelihood of feedback to occur in at least one of the input frequency bands.

In case a likelihood of feedback to occur in at least one of the input frequency bands is determined statically, a feedback detection unit is in general not comprised in the hearing aid device but is an external feedback detection unit. An external feedback detection can be used by e.g. a hearing care professional who uses the external feedback detection to detect which frequency regions or frequency bands comprise a high likelihood of feedback to occur. Accordingly, the hearing care professional can predefine the bundling of input frequency bands and the allocation of the input frequency bands to processing channels. In this situation the bundling is static. To determine a static likelihood of feedback to occur in at least one of the input frequency bands, a measurement of the feedback path can be considered. The feedback path can be measured by a hearing care professional e.g. during fitting of the hearing aid device. The measurement can be converted into a matrix which determines if an input frequency band is going to be bundled or not. The matrix can be the applied bundling scheme.

The feedback path can be modelled using an adaptive filter. The output of the adaptive filter can be subtracted from e.g. the acoustic signal received by the microphone to cancel acoustic and/or mechanical feedback picked up by the microphone. As a consequence of feedback cancellation more gain can be applied in the hearing aid. In general, a feedback cancellation filter adapts on the acoustic signal received by a microphone.

Alternatively, a semi-static scheme can be applied which can be based on a feedback measurement measured during startup of the hearing aid device. The semi-static scheme has the advantage that the most critical frequencies in terms of likelihood of feedback depend on the current hearing aid device mounting.

A signal processing unit of the hearing aid device processes the first frequency bands to be processed in the number $N_{P,1}$ of first processing channels. It can be advantageous if the number $N_{P,1}$ of first processing channels is smaller than the number $N_{I,1}$ of first input frequency bands. The processing of the input frequency bands in a smaller number of processing channels can lead to a reduced computational power and, thus, to the advantageous consequence of saving energy during device operation.

In a preferred embodiment, the processing unit provides output frequency bands that correspond to the processed input frequency bands. The output frequency bands are combined to a digital audio output signal (e.g. using a synthesis filter bank). Using a digital-to-analog converter, the digital audio output signal can be converted into an electrical audio output signal 71 that can be delivered to an output transducer.

An output transducer of the hearing aid device can be configured to convert the electrical audio output signal into a user perceivable signal, e.g. an acoustic output signal which, for a user, is perceivable as sound. The output transducer can be a speaker, receiver, a stimulation unit of a cochlear implant are any other kind of output transducer, According to the invention the first frequency band bundling and allocation unit is configured to generate a first bundling and allocation scheme which determines the bundling of the first $N_{I,1}$ input frequency bands and the allocation of the first frequency bands to be processed to the first $N_{P,1}$ processing channels. The first bundling and allocation scheme depends on the likelihood of feedback to occur in at least one of the first $N_{I,1}$ input frequency bands.

The inventors recognized that if a frequency band comprises a high likelihood of feedback to occur it can be advantageous to have a high frequency resolution in that frequency region. This means that input frequency bands in the frequency region are not bundled. If a frequency band has a high likelihood of feedback to occur, it is desirable to apply only little or no gain to the respective frequency band. Consequently, feedback can be reduced or suppressed in an efficient manner. In contrast, it might be desirable to apply higher gain to frequency bands that are not subject to a high likelihood of feedback. Moreover, frequency bands that comprise a lower likelihood of feedback to occur can be bundled. As a consequence, the input frequency bands can be processed in a smaller number of frequency bands such that the computational effort and, thus, the energy consumption of the hearing aid device can be reduced.

The bundling and allocation scheme is stored in the memory unit and can be adjusted dynamically or statically or semi-statically. The bundling and allocation scheme determines if a frequency band of the number of $N_I$ input frequency bands shall be bundled or not. Accordingly, feedback can be counteracted in a very efficient manner by maintaining a high frequency resolution in the frequency region of a frequency band that comprises a high likelihood of feedback to occur. At the same time, the energy consumption can be reduced because in frequency regions which comprise frequency bands with a smaller likelihood of feedback to occur can be bundled.

Sometimes feedback is also referred to as howl. Moreover, one could also use the term distance to feedback limit instead of likelihood of feedback to occur. The term distance to feedback expresses how much more gain can be applied until reaching the maximum allowable gain before the hearing aid device is too close to feedback or before the sound quality of an acoustic output signal. The maximum allowable gain depends on the measured feedback path and the currently applied gain.

An alternative definition of a likelihood of feedback is provided by using the term gain margin, which is the amount of gain left before resulting in feedback. For example, a gain margin of e.g. 3 dB means that 3 dB more can be applied before resulting in feedback.

The hearing aid device may optionally further comprise a first frequency band redistribution unit that is configured to redistribute the $N_{P,1}$ processing channels to a number $N_{O,1}$ of first output frequency bands. After processing the number of input frequency bands in a smaller number of processing channels, the processed frequency bands are redistributed to a larger number of output frequency bands. Consequently, the frequency resolution can be increased again compared to the number of processing channels.

In a preferred embodiment the first bundling and allocation scheme is a two-dimensional matrix representing the number $N_{I,1}$ of first input frequency bands and the number $N_{P,1}$ of first processing channels wherein for each of the $N_{I,1}$ input frequency bands, the two-dimensional matrix includes a bundling value.

If the likelihood of feedback is above the threshold the bundling value can e.g. be zero and the respective input frequency band is not bundled within the $N_{P,1}$ processing channels, and if the likelihood of feedback is below the threshold the bundling value can e.g. be one and the respective input frequency band is bundled within the $N_{P,1}$ processing channels. The likelihood of feedback to occur in at least one of the input frequency bands can be detected e.g. either by a feedback detection unit that is comprised in the hearing aid device or by an external feedback detection unit. The threshold may be predefined, e.g. during a fitting session, or adaptively determined, during use of the hearing device. The threshold may be frequency dependent, e.g. dependent on a user's hearing profile (need for amplification), the hearing device style (open or closed), etc.

The bundling value could be between zero and one.

The frequency band bundling and allocation unit may be configured to dynamically adapt the number NP,1 of first processing channels and/or the number NP,2 of second processing channels during normal use of the hearing aid device. A consequence of an adaptive bundling is that the instrument is adaptively re-calibrated. E.g. internal level estimates depend on the bundling scheme. Calculating a level of a frequency band, when adding two frequency bands, then the level increases, and in order to prevent the change in level a re-calibration of the level is needed. Alternatively, a fixed number of bundling schemes could be stored in the instrument along with the corresponding calibrating values.

The bundling and allocation scheme can be a two-dimensional matrix comprising ones and zeroes, where ones define a band to be bundled and zeroes defines bands not to be bundled.

For example, a column can define the processing channels $N_P,1$ and a row can define input frequency bands $N_I$ or vice versa. Thus, the bundling and allocation scheme determines which of the input frequency bands shall be bundled and/or allocated based on a likelihood of feedback to occur the respective input frequency band.

The signal processing unit can optionally be configured to determine a first filter coefficient for each of the $N_{I,1}$ input frequency bands based on the first bundling and allocation scheme, and wherein the acoustic output signal comprises a summation of the filter coefficients each multiplied by the respective of the $N_{O,1}$ output frequency bands. The filter coefficients are determined such that the feedback response between the microphone and the speaker is reduced. Each filter coefficient includes an imaginary part and a real part. The imaginary part can be determined in a way that the feedback response is reduced as much as possible without affecting the inherent speech information or with as little distortion of the inherent speech information as possible. In case that there is more than one microphone comprised in the hearing aid, each microphone comprises its individual set of input frequency bands which are bundled, allocated to processing channels and subsequently processed in the signal processing unit.

By introducing complex filter coefficients to the filter bank makes the bundling relevant for time-domain bandpass filters.

Preferably, the number of Ni input frequency bands is the same as the number of No output frequency bands.

In a preferred embodiment of the invention the hearing aid device comprises
- a second microphone configured to receive a second acoustic signal and to convert the second acoustic signal to a second electrical audio signal,
- a second analog-to-digital converter for converting the second electrical audio signal into a second time-domain input signal,
- a second input unit comprising a second analysis filter bank which is configured to convert the second time-domain input signal to a number $N_{I,2}$ of second input frequency bands wherein the number $N_{I,2}$ of second input frequency bands is determined by the second analysis filter bank, a second frequency band bundling and allocation unit which is configured to bundle adjacent second input frequency bands and to allocate second frequency bands to be processed to a number $N_{P,2}$ of second processing channels, wherein the memory unit is configured to store data indicating which of the second $N_{I,2}$ input frequency bands is subject to a likelihood of feedback that is above the threshold, and wherein the signal processing unit is adapted to process the second input frequency bands to be processed in the number $N_{P,2}$ of second processing channels, and where the number $N_{P,2}$ of second processing channels is smaller than the number $N_{I,2}$ of second input frequency bands, and wherein the second frequency band bundling and allocation unit is configured to generate a second bundling and allocation scheme which determines the bundling of the second $N_{I,2}$ input frequency bands and the allocation of the second frequency bands to be processed to the second $N_{P,2}$ processing channels based on the likelihood of feedback to occur in at least one of the second $N_{I,2}$ input frequency bands. The first and second microphones create a directional system. The directional system can be configured such that the directional pattern aims at cancelling the feedback path. This means that the directional response has its minimum directivity towards the feedback path.

The hearing aid device may further comprise a second frequency band redistribution unit that is configured to redistribute the $N_{P,2}$ processing channels to a number $N_{O,2}$ of second output frequency bands. In this embodiment, the signal processing unit may be configured to determine a second set of filter coefficients for each of the second $N_{I,2}$ input frequency bands based on the second bundling and allocation scheme. The first filter coefficients of the first set of filter coefficients and the second filter coefficients of the second set of filter coefficients comprise a real part and an imaginary part. The imaginary part of the first and second filter coefficients is determined such that the likelihood of feedback to occur is minimised and such that the impact on the part of the acoustic output signal which does not comprise feedback is minimum. The acoustic output signal comprises a summation of the respective first filter coefficients each multiplied by the respective of the first $N_{O,1}$ output frequency bands and the second filter coefficients each multiplied by the respective of the second $N_{O,2}$ output frequency bands. In other words, the hearing aid device may comprise a beamformer filtering unit for providing a beamformed signal (in spatially filtered frequency sub-bands) based on said first and second output frequency bands. The beamformed signal may be further processed (e.g. to apply frequency dependent amplification or attenuation to the spatially filtered frequency sub-bands, e.g. to compensate for a user's hearing impairment) or presented to a user via electrodes implanted in the auditory nerve, or converted to a time-domain audio output signal by a synthesis filter bank for presentation to user via a speaker or via a vibrator of a bone-conduction hearing aid.

Having two microphones, each of the microphones may be bundled differently if the feedback path of each microphone is not the same.

In a binaural hearing aid system, one or more microphones in each hearing aid may have different or same bundling scheme.

If the analysis filter bank is defined in the time-domain, filter coefficients are used. In contrast, if the analysis filter bank is defined in the frequency domain, complex weights are used. Alternatively, the frequency resolution within a frequency band can be increased using complex filter coefficients instead of a single complex weight.

Applying spatial filtering in the frequency bands to be processed allows reducing feedback. For that reason, it is advantageous to have the highest frequency resolution in frequency regions that comprise at least one frequency band with a high likelihood of feedback. In frequency regions with frequency bands that comprise a high likelihood of feedback, spatial filtering of the respective frequency bands is the more efficient for counteracting feedback if the frequency band is narrow.

In a preferred embodiment, the likelihood of feedback is determined by a feedback detection unit which is comprised in the hearing aid device or which is comprised by an external device. In case the feedback detection unit is comprised in the hearing aid device, it is possible to dynamically update the bundling and allocation scheme according to changing feedback situations. If the feedback detection unit is not comprised within the hearing aid device but is configured as an external feedback detection unit, it is possible to install a static bundling and allocation scheme.

In a preferred embodiment, the feedback detection unit is configured to determine the likelihood of feedback between the output of the speaker and the input of the first microphone defining a first feedback path and between the output of the speaker and the input of the second microphone defining a second feedback path. If the hearing aid device comprises two microphones each microphone can be subject to feedback independent of the other. The first and second microphones receive first and second acoustic signals that are converted to first and second electrical audio signals, respectively. The first and second analog-to-digital converters convert the first and second audio signals into first and second time-domain input signals, respectively. Accordingly, the first and second input units convert the first and second time-domain input signals to a number of first and second frequency bands, respectively. To dynamically determine whether at least one of the first and second input frequency bands comprises a high likelihood of feedback, a first and second feedback path can be determined. The memory unit stores data indicating which of the first and second input frequency bands are subject to a likelihood of feedback that is above a (e.g. predefined) threshold. Subsequently, the first and second frequency bundling and allocation units bundle the first and second input frequencies according to a first and second bundling and allocation scheme.

The feedback detection unit can optionally be configured to dynamically determine the likelihood of feedback to occur in at least one of the first $N_{I,1}$ input frequency bands and/or in at least one of the second $N_{I,2}$ input frequency bands, and wherein the first frequency band bundling and allocation unit and/or the second frequency band bundling and allocation unit is/are configured to dynamically control the bundling and allocation of the first $N_{I,1}$ input frequency bands and/or of the $N_{I,2}$ second input frequency bands, respectively.

If the feedback situation changes over time, changing frequency bands may comprise a high likelihood of feedback. The bundling and allocation scheme can be dynamically adjusted to these changes. Accordingly, bundling of first and second frequency bands can be dynamically controlled by the first and second frequency bundling and allocation units, respectively.

The feedback detection unit can preferably further be configured to perform adaptive feedback cancellation to counteract acoustic feedback on the basis of acoustic signals detected by the first microphone and/or the second microphone.

Already at the stage of the feedback detection unit feedback, feedback cancellation can be performed using adaptive feedback cancellation.

In a preferred embodiment, the feedback detection unit is configured to adaptively track feedback path changes over time based on a linear time invariant filter which are adapted to estimate the first and/or the second feedback path wherein first and/or the second filter coefficients are updated over time.

If feedback path changes can be tracked over time, the bundling and allocation scheme stored in the memory unit can be dynamically updated. As a result, the performance of the hearing aid device can be improved with respect to continuously changing hearing situations. At the same time, frequency bands that do not comprise a high likelihood of feedback can be bundled. Consequently, a smaller number of frequency bands is actually processed leading to the advantageous result that the computational effort needed is reduced. This may lead to a reduced power consumption during use of the hearing aid device.

In a preferred embodiment, the frequency band bundling and allocation unit is configured to dynamically adapt the number $N_{P,1}$ of first processing channels and/or the number $N_{P,2}$ of second processing channels during normal use of the hearing aid device.

The dynamical adaptation of the number of first and second processing channels during normal use of the hearing aid device leads to an improved hearing experience as the likelihood of feedback to occur in at least one of the first and second frequency bands is continuously tracked and reduced by applying a filter to the respective frequency band. Moreover, due to the bundling of frequency bands having only a small likelihood of feedback the computational power is reduced leading to the advantage that the hearing aid device can be used for a longer time before it is necessary to change the battery.

The first and/or the second frequency band bundling and allocation unit can be configured to allocate the first and/or the second input frequency bands, respectively, to the respective first and/or second processing channels according to a user's hearing impairment.

In a preferred embodiment, the signal processing unit is further configured to process speech intelligibility information, and wherein the signal processing unit is further configured to prioritize the processing of the first and second frequency bands to be processed either towards cancelling noise and improving speech intelligibility or towards cancelling feedback in frequency bands where only little speech intelligibility improvement is expected.

In a preferred embodiment of the previous embodiment, the signal processing unit is further configured to prioritize the processing of the frequency bands based on the measured first and/or second feedback path(s) and a speech intelligibility index.

If there exists a frequency region with a high likelihood of feedback to occur and if that region is expected to benefit only little from noise reduction, directional processing can be applied aiming at cancelling the feedback path. In frequency regions with a small likelihood of feedback to occur and which benefits from noise reduction, the directional processing can be applied aiming at improving speech intelligibility. In general, low (typically below 1000 Hz) and medium frequency regions contribute the most to the speech intelligibility such that in these frequency regions speech intelligibility can be improved by noise reduction. Moreover, the low and medium frequency regions in general comprise a lower a smaller likelihood of feedback. In contrast the higher frequency regions typically contribute less to the overall speech intelligibility. Consequently, for the higher frequency regions it can be advantageous to prioritize the directional processing towards cancelling the feedback path.

In a preferred embodiment, the first or the second or both frequency band bundling and allocation units are configured to bundle adjacent input frequency bands and to allocate the respective frequency bands to be processed for as few processing channels as necessary. If the frequency bands to be processed are processed in as few processing channels as necessary, the computational power can be reduced, and energy can be saved. The term "as few processing channels as necessary" refers to the situation where the bundling of input frequency bands is optimized towards efficiently counteracting feedback on the one hand and bundling not more frequency bands as necessary for efficiently counteracting feedback. For example, if frequency bands are bundled although the likelihood of feedback is small for the respective frequency bands, the bundling was not necessary. This situation is not optimized in the sense of the term "as new processing channels as necessary".

The hearing aid device can be a hearing instrument, a hearing aid, a bone conduction hearing aid, a headset, an earphone, an ear protection device, an active ear protection system, a handsfree telephone system, a mobile telephone, a teleconferencing system, a public address system, a karaoke system, a classroom amplification systems or a combination thereof.

The object of the invention is further achieved by a hearing aid device system comprising two or more hearing aid devices according to at least one of the previous embodiments, wherein the hearing aid devices are adapted for exchanging information about the bundling of input frequency bands, preferably via a wireless communication link.

In a preferred embodiment, the hearing aid device system can be configured to provide that the same bundling scheme is applied in both hearing aid devices of a binaural system by exchanging synchronizing control signals between the two hearing aid devices.

According to another aspect of the invention, the aforementioned object is achieved by a method of processing an input audio signal comprising receiving a first acoustic signal and converting the first acoustic signal to a first electrical audio signal
converting the first electrical audio signal into a first time-domain input signal,
converting the first time-domain input signal to a number $N_{I,1}$ of first input frequency bands wherein the number $N_{I,1}$ of first input frequency bands is determined by a first analysis filter bank,
bundling of adjacent first input frequency bands and allocating first frequency bands to be processed to a number $N_{P,1}$ of first processing channels,
storing data indicating which of the first $N_{I,1}$ input frequency bands are subject to a likelihood of feedback that is above a (e.g. predefined) threshold,
generating a first bundling and allocation scheme which determines the bundling of the $N_{I,1}$ input frequency bands and the allocation of the first frequency bands to be processed to the first $N_{P,1}$ processing channels wherein said first bundling and allocation scheme depends on the likelihood of feedback to occur in at least one of the $N_{I,1}$ input frequency bands, processing the first frequency bands to be processed in the number $N_{P,1}$ of first processing channels, wherein the number $N_{P,1}$ of first processing channels is smaller than the number $N_{I,1}$ of first input frequency bands, determining first filter coefficients for each of the $N_{I,1}$ input frequency bands based on the first bundling and allocation scheme, redistributing the $N_{P,1}$ processing channels to a number $N_{O,1}$ of first output frequency bands, and emitting an acoustic output signal into an ear of a user, wherein the acoustic output signal comprises a summation of the first filter coefficients each multiplied by the respective of the $N_{O,1}$ output frequency bands.

The summation may be replaced by a linear combination.

In a preferred embodiment of the aforementioned aspect, the method of processing an input audio signal further comprises receiving a second acoustic signal and converting the second acoustic signal to a second electrical audio signal converting the second electrical audio signal into a second time-domain input signal, converting the second time-domain input signal to a number $N_{I,2}$ of second input frequency bands wherein the number $N_{I,2}$ of second input frequency bands is determined by a second analysis filter bank, bundling of adjacent second input frequency bands and allocating second frequency bands to be processed to a number $N_{P,2}$ of second processing channels, storing data indicating which of the second $N_{I,2}$ input frequency bands are subject to a likelihood of feedback that is above a (e.g. predefined) threshold, generating a second bundling and allocation scheme which determines the bundling of the $N_{I,2}$ input frequency bands and the allocation of the second frequency bands to be processed to the second $N_{P,2}$ processing channels wherein said second bundling and allocation scheme depends on the likelihood of feedback to occur in at least one of the $N_{I,2}$ input frequency bands, processing the second frequency bands to be processed in the number $N_{P,2}$ of second processing channels, wherein the number $N_{P,2}$ of second processing channels is smaller than the number $N_{I,2}$ of second input frequency bands, determining second filter coefficients for each of the $N_{I,2}$ input frequency bands based on said second bundling and allocation scheme, redistributing the $N_{P,2}$ processing channels to a number $N_{O,2}$ of second output frequency bands, and emitting an acoustic output signal into an ear of a user, wherein the acoustic output signal comprises a summation of the first filter coefficients each multiplied by the respective of the first $N_{O,1}$ output frequency bands and the second filter coefficients each multiplied by the respective second of the $N_{O,2}$ output frequency bands.

The number $N_{P,2}$ of second processing channels may be the same as the number $N_{P,1}$ of first processing channels.

The likelihood of feedback may depend on the measured feedback path to each of the microphones, as it is desirable that the same bundling scheme is applied to each microphone. Otherwise, it becomes difficult to combine the two microphone signals.

In a preferred embodiment, a data processing system comprises a processor and program code means, adapted to cause the processor to perform the steps of the method of at least one of the two aforementioned aspects.

A cochlear implant may comprise at least one input transducer for capturing incoming sound and for generating electric audio signals which represent frequency bands of the incoming sound, a sound processor which is configured to analyze and to process the electric audio signals, a transmitter that sends the processed electric audio signals, a receiver/stimulator, which receives the processed electric audio signals from the transmitter and converts the processed electric audio signals into electric pulses, an electrode array embedded in the cochlear comprising a number of electrodes for stimulating the cochlear nerve with said electric pulses, a control unit configured to control the distribution of said electric pulses to the number of said electrodes.

In the cochlear implant as disclosed above the distribution of said electric pulses to the number of said electrodes is performed by applying one out of a plurality of different coding schemes wherein the applied coding scheme is selected according to characteristics of the incoming sound.

Also for cochlear implants, it can be the case that there are stimuli, where it is known that some frequency regions are not used. An example is a telephone conversation, where the signal is band-limited up to around 3500 Hz. Given this information, one could encode the electrodes available according to a specific hearing situation. Using the example of a telephone conversation, the telephone signal could be distributed to a number of electrodes in a different way than in other hearing situations.

For example, it could be beneficial to use all available electrodes or to increase the stimulation rate in case that not all frequencies need to be stimulated. However, an adaptation to different hearing situations requires that different coding schemes can be applied. It may also be reasonable to apply a stimuli-specific coding scheme for listening to music.

In the cochlear implant the sound processor can optionally be configured to analyze the characteristics of the incoming sound.

In a preferred embodiment of the cochlear implant, the control unit is configured to distribute the electric pulses to the number of electrodes according to a coding scheme for a telephone conversation and/or according to a coding scheme for listening to music and/or according to further coding schemes.

In a preferred embodiment of the cochlear implant, the coding scheme for listening to music is configured such that high frequency channels convey rhythm and low frequency channels resolve tonal information. Typically, currently used coding schemes are optimized towards understanding speech. This requires that a lot of information is encoded in the envelope. However, one could imagine encoding music information in a different way e.g. by using high frequency bands to convey rhythm rather than spreading it across all bands and low frequency bands to resolve tonal information.

The sound processor in the cochlear implant can optionally be configured to analyze the electric audio signals which represent frequency bands of the incoming sound with respect to an information content and to process only frequency bands that contain meaningful information such that a smaller number of electrodes than the total number of electrodes available is used for stimulating the cochlear nerve.

In a preferred embodiment of the cochlear implant the audio processing device is configured to activate a power saving mode in which the incoming sound is analyzed by the sound processor and only frequency bands of the incoming sound that contain meaningful information are transmitted to the electrodes. In order to reduce power consumption of the cochlear implant, some channels of the cochlear implant could be turned off depending on an input channel. If an acoustic input signal contains reduced or only little information above e.g. 3 kHz, the processing above 3 kHz could be turned off in order to save power. Accordingly, a smaller number of electrodes could be used for stimulating the cochlear nerve. Alternatively, if the battery of the cochlear implant is getting low, a special power saving mode could be activated, in which the acoustic input signal is analysed and only frequency bands that contain a certain information content (i.e. modulated signals) are delivered to the electrodes.

In a preferred embodiment of the cochlear implant the power saving mode is configured to use preferably 1-2 broad frequency bands which in case that the incoming sound is above a predefined amplitude threshold are transmitted to preferably 1-2 electrodes to convey a modulation for sound awareness. The described scenario refers to an extreme power saving mode in which only 1-2 broad bands are used and mapped to 1-2 electrodes to convey a modulation for sound awareness and only if the received acoustic input signal is above a predefined threshold level.

The entering of the cochlear implant into the power saving mode may be depended on a user's interaction or reaction to an incoming sound to the one or more microphones, such as head movement or a reply captured by the microphone(s).

The control unit can optionally be configured to control the distribution of electric pulses to the number of electrodes such that electric pulses are delivered to at least every second electrode in order to reduce frequency channel interactions. By simulating on every second electrode only channel interactions can be reduced. As a consequence, in this stimulation mode a user needs to adapt to a specific frequency map that is different to a commonly used program.

In a preferred embodiment of the cochlear implant, at least one wall channel is provided to reduce channel interactions, wherein the wall channel is a channel in which no signal is presented and which is adjacent to the edge of a channel in which a signal is presented. In order to give an increased band-limited auditory nerve response, a so-called wall channel can be introduced which can be adjacent to the edge of the band in which a respective signal is presented. For example, the wall channel could be the next band above 3.5 kHz when a user is in a telephone conversation. The idea behind this is to inhibit a spread of excitation into high-frequency regions which, lacking their own stimulus, might respond more readily to stimulation from lower-frequency electrodes. In essence, one may find that high-frequency auditory nerve fibres encode a highly degraded version of an edge frequency band. This might be confusing or distracting for a user.

In a preferred embodiment of the cochlear implant, a wall channel stimulus within the wall channel is a low-level pulse, preferably a sub-threshold pulse or a supra-threshold pulse. As a consequence of a wall channel being a low-level pulse, a response adjacent to the passband is created that is low enough in level to be of little or of no perceptual relevance and that occupies respective neurons, such that they do not respond much to spread of excitation from lower-frequency electrodes.

Two or more cochlear implants according to at least one of aforementioned embodiments of the cochlear implant can also be comprised in a cochlear implant system, wherein the cochlear implants can be adapted for exchanging information about the applied coding scheme. Preferably the exchange of information is provided via a wireless communication link.

In a preferred embodiment of the cochlear implant system the cochlear implant system can be configured to provide that the same coding scheme is applied in both cochlear implants of a binaural system by exchanging synchronizing control signals between the two cochlear implants.

BRIEF DESCRIPTION OF DRAWINGS

The objects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each object may each be combined with any or all features of the other objects. These and other objects, features and/or technical effect will be apparent from and elucidated with reference to the illustrations described hereinafter in which:

FIG. 2: schematically shows the processing steps of an acoustic signal received by one microphone;

FIG. 3: schematically shows the processing steps of acoustic signals received by two microphones;

DETAILED DESCRIPTION

Figure 1:
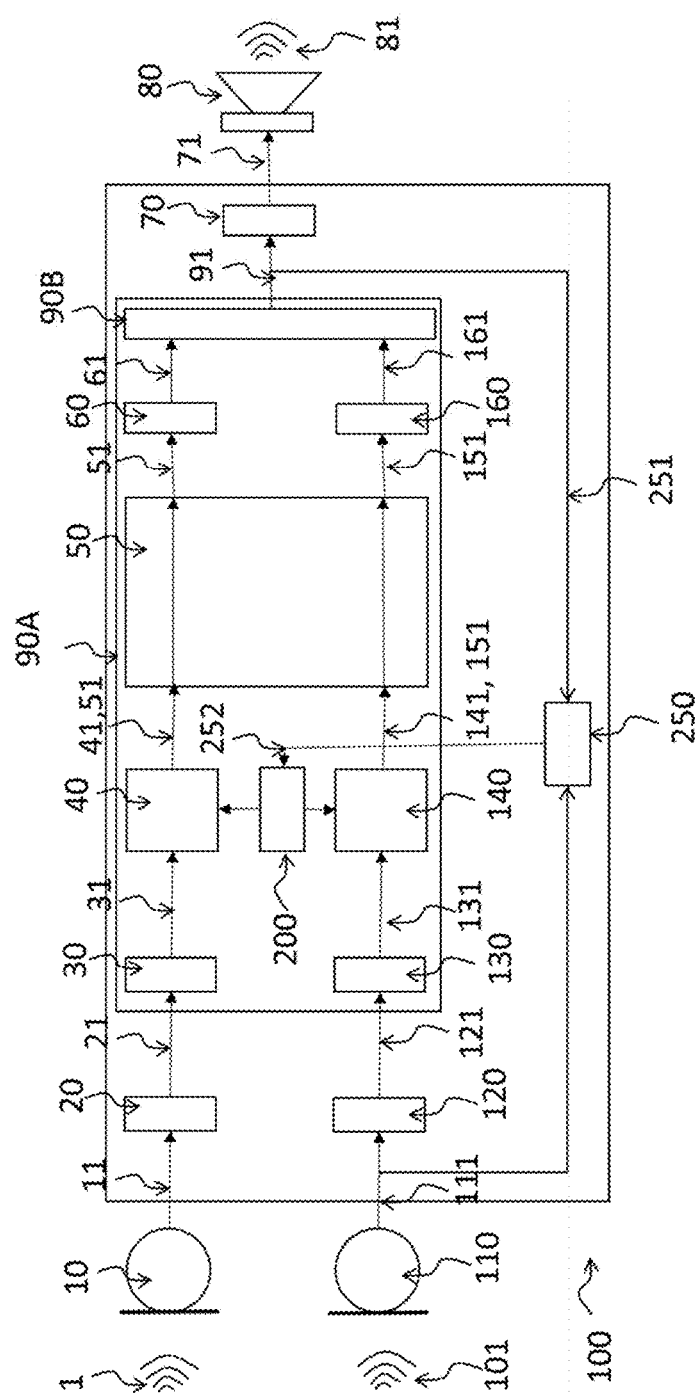
FIG. 1: shows a sketch of a hearing aid device.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several object of the hearing device system and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals or with a receiver/loudspeaker arranged close to or in the ear canal such as in a Behind-the-Ear type hearing aid or a Receiver-in-the Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A hearing device may be part of a "hearing system", which refers to a system comprising one or two hearing devices, disclosed in present description, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefiting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input section such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input section may include multiple input microphones, e.g. for providing direction-dependent audio signal processing. Such directional microphone system is adapted to enhance a target acoustic source among a multitude of acoustic sources in the user's environment. In one object, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

It should be appreciated that reference throughout this specification to "one embodiment" or "an embodiment" or "an object" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various objects described herein. Various modifications to these objects will be readily apparent to those skilled in the art, and the generic principles defined herein may be applied to other objects.

The claims are not intended to be limited to the objects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follows.

FIG. 1 shows a sketch of a hearing aid device comprising a first microphone 10 configured to receive a first acoustic signal 1 and a second microphone 110 configured to receive a second acoustic signal 101. In an optional embodiment of FIG. 1 that is not shown, a first and second microphone is located behind the ear of a user as part of a behind-the-ear (BTE) hearing aid device. In another embodiment of FIG. 1 that is not shown, a first and second microphone is located in the ear canal of a user as part of an in-the-ear (ITE) hearing aid device. The first microphone 10 and the second microphone 110 convert the first acoustic signal 1 and the second acoustic signal 101 to a first electrical audio input signal 11 and a second electrical audio input signal 111, respectively.

The hearing aid device further comprises a first analog-to-digital 20 for converting the first electrical audio input signal 11 into a first time-domain input signal 21 and a second analog-to-digital converter 120 for converting the second electrical audio input signal 111 into a second time-domain input signal 121. The first 21 and second 121 time-domain signals are subsequently delivered to a digital signal processing unit 90A. The digital signal processing unit 90A comprises a first input unit 30 and a second input unit 130. The first input unit 30 is configured to convert the first time-domain input 21 signal to a number $N_{I,1}$ of first input frequency bands 31. Thereby, the number $N_{I,1}$ of first input frequency bands 31 is determined by a first analysis filter bank that is comprised in the first input unit 30. The second input unit 130 is configured to convert the second time-domain input 121 signal to a number $N_{I,2}$ of second input frequency bands 131. Thereby, the number $N_{I,2}$ of second input frequency bands 131 is determined by a second analysis filter bank that is comprised in the second input unit 130.

The hearing aid device further comprises first and second frequency band bundling and allocation units 40, 140. The first frequency band bundling and allocation unit 40 is configured to bundle adjacent first input frequency bands 31 and to allocate first frequency bands to be processed 41 to a number $N_{P,1}$ of first processing channels 51. The second frequency band bundling and allocation unit 140 is configured to bundle adjacent second input frequency bands 131 and to allocate second frequency bands to be processed 141 to a number $N_{P,2}$ of second processing channels 151.

The bundling of first input frequency bands 31 and second input frequency bands 131 can be based and a first bundling scheme and a second bundling scheme that are created based on data stored in the memory 200. The data indicate which of the first $N_{I,1}$ input frequency bands 31 and which of the second $N_{I,2}$ input frequency bands 131 are subject to a likelihood of feedback that is above a predefined threshold. In a preferred embodiment of FIG. 1 that is not shown, a hearing aid device comprises two memory units that either store data indicating which of the first input frequency bands or which of the second input frequency bands are subject to a likelihood of feedback that is above a predefined threshold.

The first frequency bands to be processed 41 and the second frequency bands to be processed 141 are delivered to a signal processing unit 50. The signal processing unit 50 is configured to process the first frequency bands to be processed 41 in the number $N_{P,1}$ of first processing channels 51 and to process the second frequency bands to be processed 141 in the number $N_{P,2}$ of second processing channels 151. Here it is preferred that the number $N_{P,1}$ of first processing channels 51 is smaller than the number $N_{I,1}$ of first input frequency bands 31, and that the number $N_{P,2}$ of second processing channels 151 is smaller than the number $N_{I,2}$ of second input frequency bands 131. The number of first and second processing channels, $N_{P,1}$, $N_{P,2}$, may be equal or different. The processing of the input frequency bands in a smaller number of processing channels can lead to the advantage, that the computational power can be reduced. A reduced computational power can lead to the advantage that the power consumption of a hearing aid device can be reduced, or the limited number of NP frequency bands can be used in the most efficient way.

The hearing aid device 100 further comprises a first frequency band redistribution unit 60 and a second frequency band redistribution unit 160. The first frequency band redistribution unit 60 is configured to redistribute the $N_{P,1}$ processing channels 51 to a number $N_{O,1}$ of first output frequency bands 61 and the second frequency band redistribution unit 160 is configured to redistribute the $N_{P,2}$ processing channels 151 to a number $N_{O,2}$ of second output frequency bands 161. Thereby, the number $N_{O,1}$ of first output frequency bands 61 can be larger than the number $N_{P,1}$ of first processing channels 51 and the number $N_{O,2}$ of second output frequency bands 161 can be larger the number $N_{P,2}$ of second processing channels. The number of first and second output frequency bands, $N_{O,1}$, $N_{O,2}$, may be equal or different.

The first output frequency bands 61 and the second output frequency bands 161 are delivered to a signal combination unit 90B, where the first and second frequency bands are combined (e.g. on a frequency band level (e.g. by forming a (possibly weighted) sum of the first and second output frequency bands) and converted (e.g. by a synthesis filter bank) to a digital audio output signal 91 (in the time-domain) and delivered to a digital-to-analog converter 70.

In an embodiment, the signal combination unit 90B comprises a beamformer filtering unit, and/or a synthesis filter bank providing a resulting spatially filtered signal by applying (possibly) complex (frequency dependent) beamformer weights to the respective first and second electric audio signals. The beamformer filtering unit may e.g. be configured to provide a beamformer that is minimally sensitive in a direction towards the origin of feedback (the speaker) in frequency regions where feedback is likely to occur (using a higher frequency resolution in this frequency region according to the present disclosure) and to (e.g. adaptively) minimize (other) noise in other frequency regions. Alternatively, all frequency bands may be directed to feedback cancellation (e.g. always, or in situations where feedback is estimated to be present, e.g. severe). In an embodiment, the beamformer filtering unit may be configured to cancel feedback (echo) in a low frequency region, e.g. below 1 kHz (e.g. in a specific echo cancelling mode, e.g. in a telephone mode, where sound is picked up by the hearing device and transmitted to a far end listener and where sound from the far end listener is received by the hearing device).

Using a digital-to-analog converter 70, the digital audio output signal 91 is converted into an (analog) electrical audio output signal 71 that is delivered to a speaker 80. The speaker 80 is configured to transmit an acoustic output signal 81 that is based on an electrical audio output signal 71 into an ear of a user of the hearing aid device 100. In a preferred embodiment of FIG. 1 that is not shown, a speaker is placed in the ear canal of a user.

In a preferred embodiment of FIG. 1 that is not shown, units of the same kind such as a first and a second input unit are comprised in a single unit having the same functionality as the two separated units. In a preferred embodiment of FIG. 1 that is not shown, a number of units with different functionality such as e.g. an input unit and an analog-to-digital converter can be comprised in the same unit that performs the functionality of the comprised individual units. In an alternative embodiment of FIG. 1 that is not shown, only one microphone is comprised such that either the upper branch or the lower branch shown in FIG. 1 are comprised in the alternative embodiment. The individual branch of the alternative embodiment of FIG. 1 still comprises a memory unit with the functionality of the memory unit 200 shown in FIG. 1.

As stated above, the memory unit is configured to store data indicating which of the first $N_{I,1}$ input frequency bands and second $N_{I,2}$ input frequency bands are subject to a likelihood of feedback that is above a predefined threshold. Moreover, the likelihood of feedback is stored in a first and second bundling scheme that can be a two-dimensional matrix indicating if a first and/or a second input frequency band shall be bundled or not. This allows to implement a bundling scheme yielding that the frequency resolution in frequency regions comprising frequency bands with a high likelihood of feedback is larger compared to frequency regions that comprise frequency bands with a smaller likelihood of feedback to occur. If the frequency resolution in frequency regions is high, it is possible to reduce or counteract the feedback in the respective frequency bands very efficiently. This is due to the fact that the respective frequency bands can be selected and processed individually and a filter be exclusively applied to these respective frequency bands. Moreover, frequency bands with a small likelihood of feedback to occur can be bundled such that the computational effort and thus the power consumption of the hearing aid can be reduced.

The likelihood of feedback to occur in at least one of the first and/or second frequency bands can be determined by a feedback detection unit 250. The feedback detection unit 250 detects the likelihood of feedback by e.g. dynamically tracking changes in the feedback path 251. In the embodiment of FIG. 1, (only) the feedback path between the speaker 80 and the second microphone 110 is estimated by feedback detection unit 250. If the detected likelihood of feedback to occur in at least one of the second input frequency bands 131 is high, the respective information is delivered 252 to the memory unit 200 and stored as data indicating which of the second $N_{I,2}$ input frequency bands are subject to a likelihood of feedback that is above a predefined threshold.

In an alternative embodiment that is not shown in FIG. 1, two feedback detection units can be comprised each working exclusively for one processing branch, only. If one or more feedback detection units are comprised in a hearing aid device, a dynamical tracking of feedback path changes can be implemented such that a first and/or a second bundling scheme can be updated during hearing aid device operation according to changing feedback situations. A first feedback detection unit can be configured to track a first feedback path between a first microphone and a speaker and a second feedback detection unit can be configured to track feedback path changes in the feedback path between the second microphone and the speaker.

In an alternative embodiment that is not shown in FIG. 1, the feedback detection unit is implemented as an external feedback detection unit. A hearing care professional can detect frequency bands that comprise a high likelihood and store data indicating which of the input frequency bands are subject to a likelihood of feedback that is above a predefined threshold on a memory unit comprised in a hearing aid device. As a result, a frequency band bundling scheme will be static.

The signal processing as described above can also be implemented in a hearing aid implant such as a cochlear implant. In this case, the processed signal would not be converted to an acoustic output signal that is emitted by a speaker but a processed electric audio signal could be converted into electric pulses. Then, an electrode array comprising a number of electrodes which are embedded in the cochlear of a user could be used for stimulating the cochlear nerve with said electric pulses.

FIGS. 2 and 3 which are explained in the following, focus on the different signal processing steps as implemented in a hearing aid device according to a preferred embodiment of the invention. FIG. 2 focuses on a hearing aid device comprising one microphone and FIG. 3 describes a hearing aid device comprising two microphones.

FIG. 2 depicts the signal processing steps in hearing aid device according to a preferred embodiment of the invention. First, a microphone 10 receives an acoustic signal 1 which is converted into a number of $N_I$ input frequency bands 31 (e.g. by an analysis filter bank, cf. e.g. 30 in FIG. 1). The input frequency bands 31 can be bundled or partly bundled and subsequently allocated to a number $N_P$ of processing channels 51 (e.g. by a frequency band bundling and allocation unit 40, as indicated in FIG. 1). The number $N_P$ of processing channels 51 are processed in the signal processing unit 50. Processing in the signal processing unit 50 can include the determination of filter coefficients or gain values (Wp) 53 for each of the $N_1$ input frequency bands based on e.g. a bundling and allocation scheme. After signal processing, the $N_P$ processing channels are redistributed to a number $N_O$ of output frequency bands (cf. NP→NO unit in FIG. 2). This allows to filter selected frequency bands that are subject to a high likelihood of feedback or to apply different gain levels to selected frequency bands according to specific hearing situations.

In the embodiment shown, the number $N_I$ of input frequency bands and the number $N_O$ of output frequency bands is identical as indicated by the arrow 35. Consequently, the initial frequency resolution is rehabilitated after processing the signal in a smaller number of processing channels $N_P$. The acoustic output signal 81 provided by the speaker 80 comprises a 'summation' of the resulting frequency sub-band signals determined from the contents of the $N_P$ processing channels (filter coefficients 53 (Wp)) subject to a frequency band redistribution unit (cf. unit 60 (or 160) in FIG. 1) and each multiplied by the respective of the $N_I$ input frequency bands 35 received from input unit 30 (providing the $N_I$ input frequency bands 31). The resulting frequency sub-band signals, output band signals 61, are converted to a time-domain output signal 71 by a synthesis filter bank (FBS) (and possibly a DA converter) and fed to speaker 80.

The signal processing as described above can also be implemented in a hearing aid implant such as a cochlear implant. In this case, the processed signal would not be converted to an acoustic output signal that is emitted by a speaker but a processed electric audio signal could be converted into electric pulses. Then, an electrode array comprising a number of electrodes which are embedded in the cochlear of a user could be used for stimulating the cochlear nerve with said electric pulses. In this case, the individual band signals (e.g. $N_P$ channel signals Wp1*No1, Wp2*No2, Wp3*No3, . . . , or $N_O$ redistributed output band signals) could be presented to a different one of the electrodes of the electrode array.

FIG. 3 depicts the signal processing steps in hearing aid device according to a preferred embodiment of the invention. In contrast to FIG. 2, a first microphone 10 and a second microphone 110 are comprised and configured to receive a first acoustic signal 1 and a second acoustic signal 101, respectively. The first acoustic audio signal 1 is converted into a number $N_{I,1}$ of first input frequency bands and the second acoustic audio signal 101 is converted into a number $N_{I,2}$ of second input frequency bands. The first input frequency bands 31 can be bundled according to a first bundling scheme and the second frequency bands 131 can be bundled according to a second bundling scheme. Subsequently, the number of first frequency bands to be processed is allocated (by unit N1p) to a number $N_{P,1}$ of first processing channels 51 and the number of second frequency bands to be processed is allocated (by unit N2p) to a number $N_{P,2}$ of processing channels 151.

The number $N_{P,1}$ of first processing channels 51 and the number $N_{P,2}$ of second processing channels 151 are processed in the signal processing unit 50. Processing in the signal processing unit 50 can include the determination of a set of first filter coefficients (W1p) 54 for each of the $N_u$ first input frequency bands and the determination of a set of second filter coefficients (W2p) 55 for each of the $N_{I,2}$ second input frequency bands based on e.g. a likelihood of feedback in at least one of the first and second input frequency bands. After signal processing, the $N_{P,1}$ first processing channels and the $N_{P,2}$ second processing channels are redistributed to a number $N_{O,1}$ of first output frequency bands and to a number $N_{O,2}$ of second output frequency bands, respectively (cf. unit NP1→NO, NP2→NO). Each of the number $N_{O,1}$ of first output frequency bands and the number $N_{O,2}$ of second output frequency bands can be multiplied by an individual (possibly complex) filter coefficient that is determined by the signal processing unit 50. This allows suppressing feedback in frequency bands comprising a high likelihood of feedback (beamforming, cf. unit WS).

The first filter coefficients of the first set of filter coefficients (W1p) and the second filter coefficients of the second set of filter coefficients (W2p) may comprise a real part and an imaginary part. The real and imaginary part of the first and second filter coefficients can be determined such that the likelihood of feedback to occur is minimised and such that the impact on the part of the acoustic output signal which does not comprise feedback is minimum (e.g. using beamforming techniques). Moreover, the acoustic output signal 81 comprises a (possibly weighted) summation of the respective first filter coefficients each multiplied by the respective of the first $N_{O,1}$ output frequency bands and the second filter coefficients each multiplied by the respective of the second $N_{O,2}$ output frequency bands. The output frequency bands may be received (35A and 35B) from the first input frequency bands 31 and the second input frequency bands 131, respectively. The resulting frequency output bands 61 may be translated to the time-domain (signal 71) by a synthesis filter bank FBS (and possibly converted to an analog signal by DA converter) before presentation to the speaker 80.

The filter coefficients could have different purpose depending on the amount of feedback in the feedback path 250: In frequency bands with high risk of feedback, the coefficients are adapted towards minimizing feedback. In bands, where the risk of feedback is small (e.g. depending on a feedback path measurement, e.g. at low frequencies), the coefficients could be adapted towards minimizing external noise. In certain application scenarios involving large delays from output to input, echo cancellation can appear at relatively low frequencies. In such cases, the coefficients may be used to minimize echo in low frequency bands, e.g. below 1.5 kHz or below 1 kHz.

The signal processing as described above can also be implemented in a hearing aid implant such as a cochlear implant. In this case, the processed signal would not be converted to an acoustic output signal that is emitted by a speaker but a processed electric audio signal could be converted into electric pulses. Then, an electrode array comprising a number of electrodes which are embedded in the cochlear of a user could be used for stimulating the cochlear nerve with said electric pulses (each e.g. representing contents of a different output channel or band).

Figure 4:
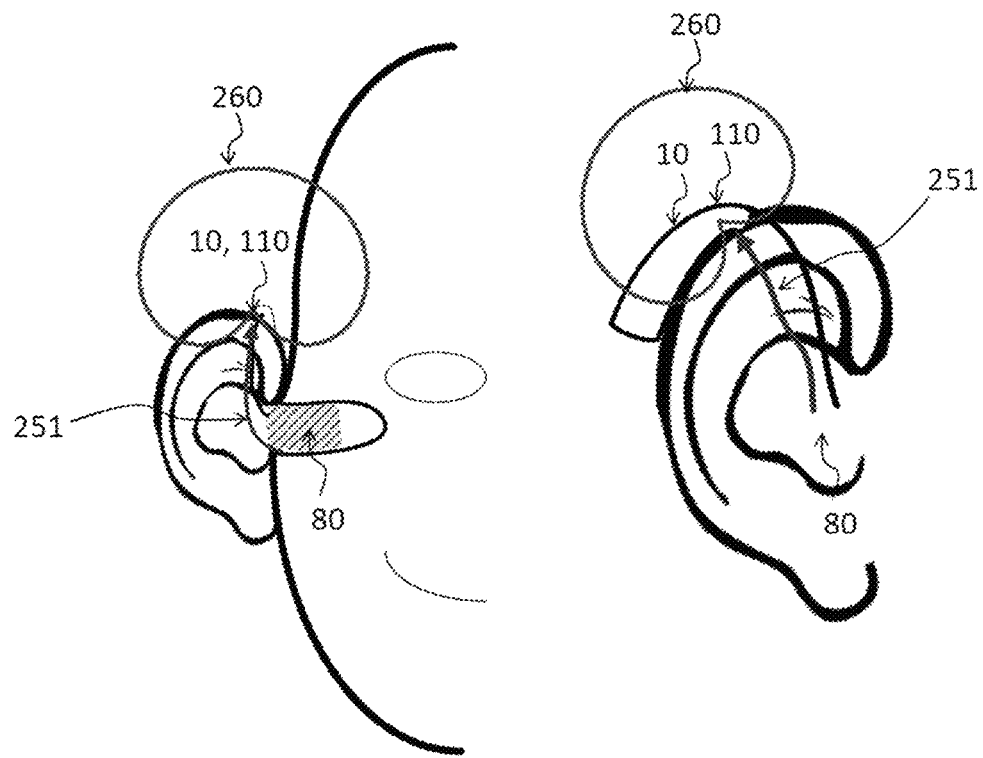
FIG. 4: illustrates the feedback path and the directional pattern of a behind-the-ear (BTE) hearing aid device.

FIG. 4 shows a behind-the-ear (BTE) microphone containing two microphones. In case a hearing aid device contains two microphones, the directional system can be adapted towards cancelling the estimated feedback path 251. The feedback paths are related to the distance between the first or the second microphone 10,110 and the speaker 80. For a given frequency band, a directivity pattern 260 can be improved towards cancelling the estimated feedback path 251 while keeping a preferred listening direction unaltered. The left part of FIG. 4 represents front view of (a right part of the head of) a user wearing an embodiment of a (BTE-type) hearing device at the right ear, whereas the right part represents a side view of the hearing device at the right ear. The embodiment may represent a receiver in the ear (RITE) style hearing device, where the speaker (receiver) is located in the ear canal or a BTE style hearing device, where the speaker (receiver) is located in the BTE-part, and where sound is propagated to the ear canal by a tube between the BTE-part and the ear canal, c£ bold line. In the embodiments shown, the directional response has its minimum directivity towards the feedback path 251. In frequency regions where feedback is likely to occur, a higher frequency resolution is desirable. Consequently, the frequency band bundling as implemented by a bundling scheme can be performed such that the frequency resolution in frequency regions with high likelihood of feedback is high.

At least one of the microphones (10, 110) may be used as a reference microphone for estimating feedback (cf. e.g. FIG. 1).

Figure 5:
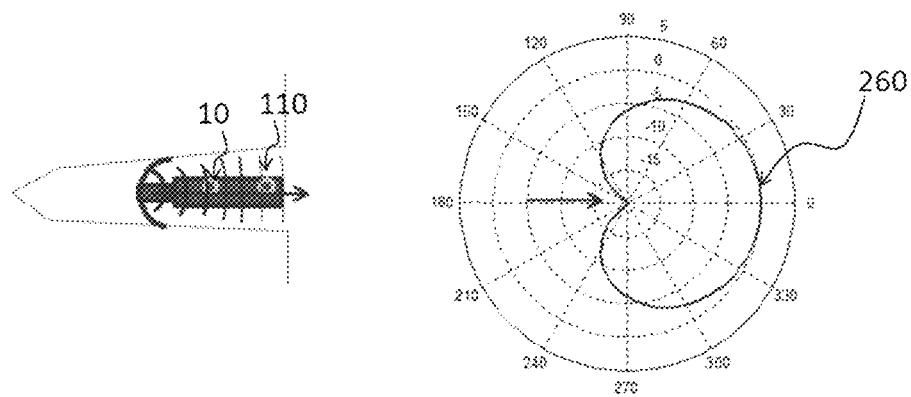
FIG. 5: illustrates the basic principle of an in-the-ear (ITE) microphone.

FIG. 5 illustrates an in-the-ear (ITE) style hearing device comprising a dual microphone solution as used for feedback cancellation. A hearing aid device containing two microphones 10, 110 which are placed in the ear canal of a user (cf. left part of FIG. 5) can be even better suited for cancelling the feedback path compared to the BTE solution presented in FIG. 4. The two microphones 10, 110 can be spaced by about 7 to 8 millimetres. Here, a fixed or an adaptive directional gain (cf. directivity pattern 260, cf. right part of FIG. 5) can be applied aiming at counteracting at the frequencies where feedback occurs.

Figure 6:
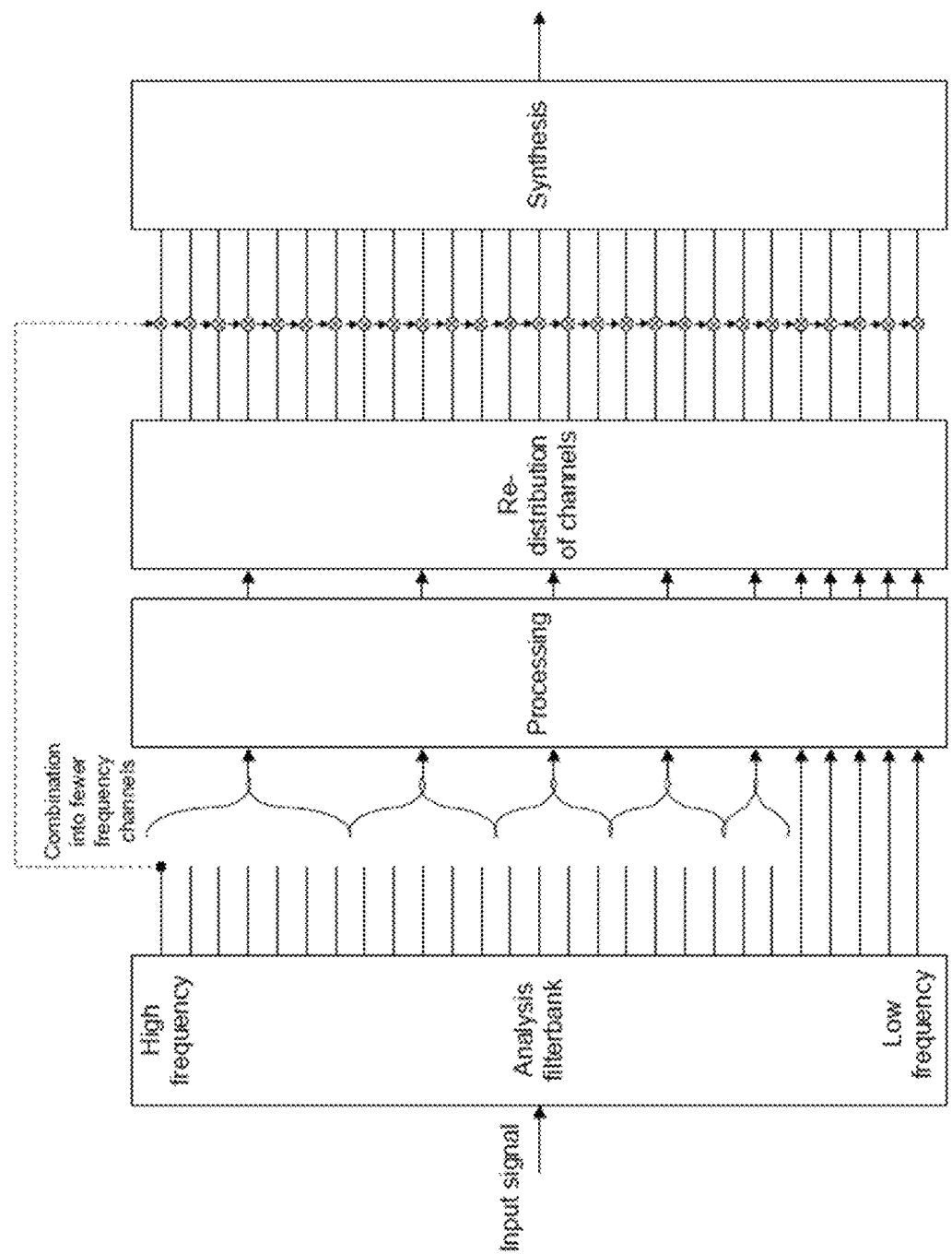
FIG. 6: exemplary depicts frequency bundling according to prior art.

FIG. 6 schematically depicts signal processing according to prior art (cf. e.g. EP2503794A1). A time-domain input signal is converted to a number of input frequency bands. The number of input frequency bands is determined by an analysis filter bank. In the example shown the frequency increases from bottom to top such that at the bottom part of the analysis filter bank low frequencies are shown and at the top part high frequencies are shown. In order to reduce the computational effort and thus to save energy, some input frequency bands are merged into a fewer number of processing channels. After processing, the processed frequency bands are redistributed to the initial number of input frequency bands. A (e.g. fixed) gain that could be complex is calculated during the processing and applied to the number of output frequency bands. Subsequently, the bands are processed via a synthesis filter bank in order to obtain a modified time-domain signal.

The signal processing as described above can also be implemented in a hearing aid implant such as a cochlear implant. Then the bundling of frequency bands could be used and applied to the distribution of electric pulses to a number of said electrodes. The distribution of electric pulses could e.g. be performed by applying one out of a plurality of different coding schemes and the applied coding scheme could be selected according to characteristics of an incoming sound.

Figure 7:
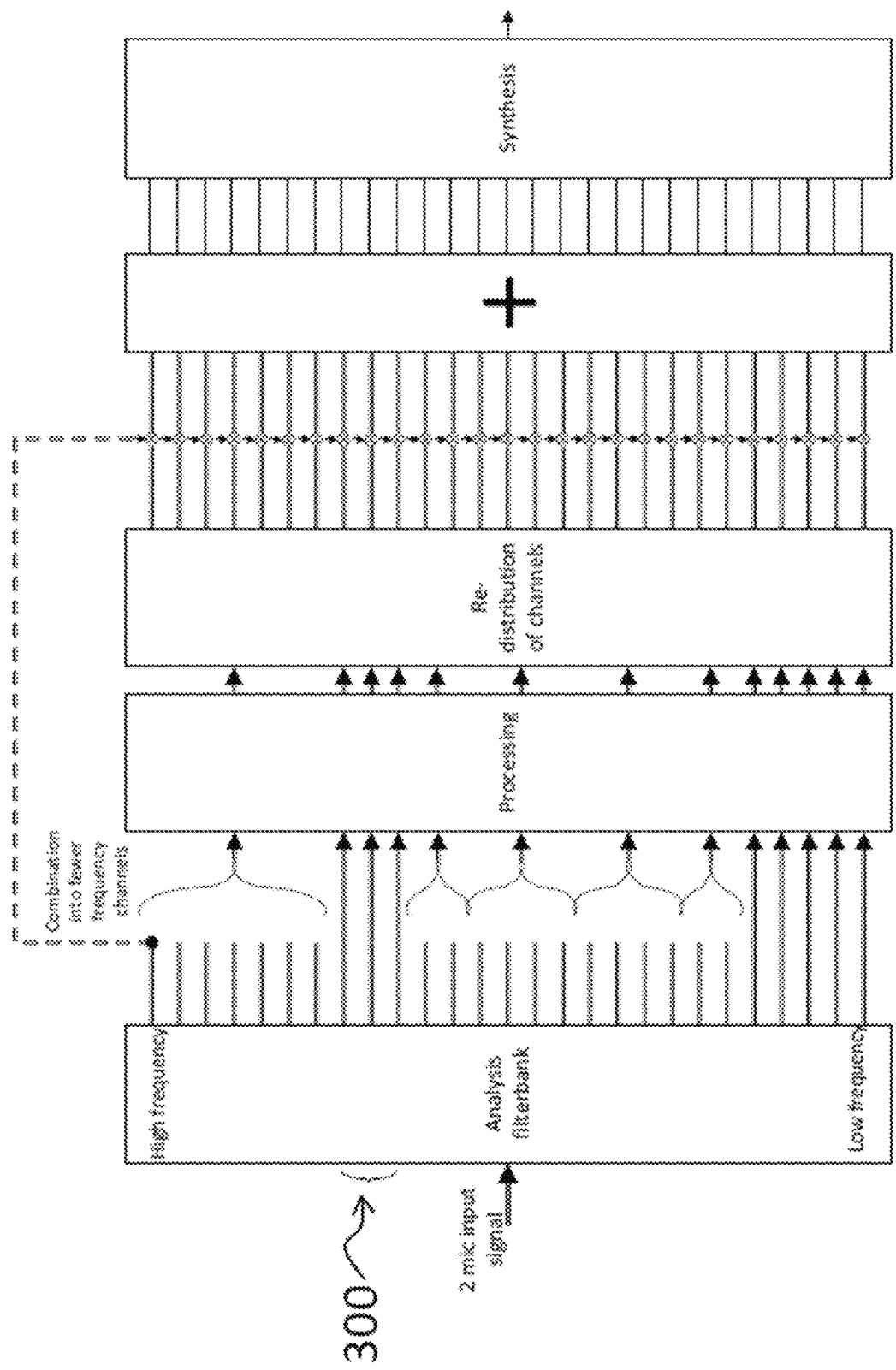
FIG. 7: exemplary depicts frequency bundling according to a likelihood of feedback to occur in respective frequency bands.

FIG. 7 schematically depicts signal processing according to a preferred embodiment of the invention. A first and a second acoustic signal received by a first and a second microphone are converted to a first and second (e.g. digitized) time-domain input signal, respectively, and delivered to an analysis filter bank (comprising first and second analysis filter banks for providing frequency sub-band versions of the first and second time-domain input signals, respectively). The frequency bands embraced by a curly bracket 300 represent frequency bands in a region with a high likelihood of feedback. As recognized by the inventors, in regions where a likelihood of feedback is high it is desirable to have a high frequency resolution in order to efficiently counteract feedback. Consequently, the frequency bands where feedback is likely to occur are not bundled and the frequency bundling is performed towards an improved cancelling of feedback. In frequency regions, where feedback is likely to occur, the directional system can be adapted towards cancelling the feedback path. In those regions which typically are the higher frequencies regions it is desirable to have a high frequency resolution.

After processing (of each of the first and second microphone signals) in a smaller number of processing channels, the processed frequency channels are redistributed to a number of output frequency bands that can be an identical number to the initial number of input frequency bands. During processing, filter coefficients (e.g. respective channel specific values) are determined and subsequently applied to each of the input frequency bands of the first and second microphone signals (cf. dashed arrow from input bands to multiplication units of each re-distributed band). In the respective multiplication units, the determined filter coefficients for each frequency band of the first and second microphone signals are mixed with the contents of each of the corresponding input frequency bands of the respective first and second microphone signals to provide first and second output frequency bands. The unit denoted '+' represents a combination of the first and second output frequency bands. The unit '+' may e.g. implement a weighted sum of the first and second output bands, e.g. to implement specific frequency (band) specific bema patterns. Subsequently, the resulting frequency sub-bands are processed via a synthesis filter bank in order to obtain a modified time-domain signal.

The signal processing as described above can also be implemented in a hearing aid implant such as a cochlear implant. Then the bundling of frequency bands could be used and applied to the distribution of electric pulses to a number of said electrodes. The distribution of electric pulses could e.g. be performed by applying one out of a plurality of different coding schemes and the applied coding scheme could be selected according to characteristics of an incoming sound.

Figure 8:
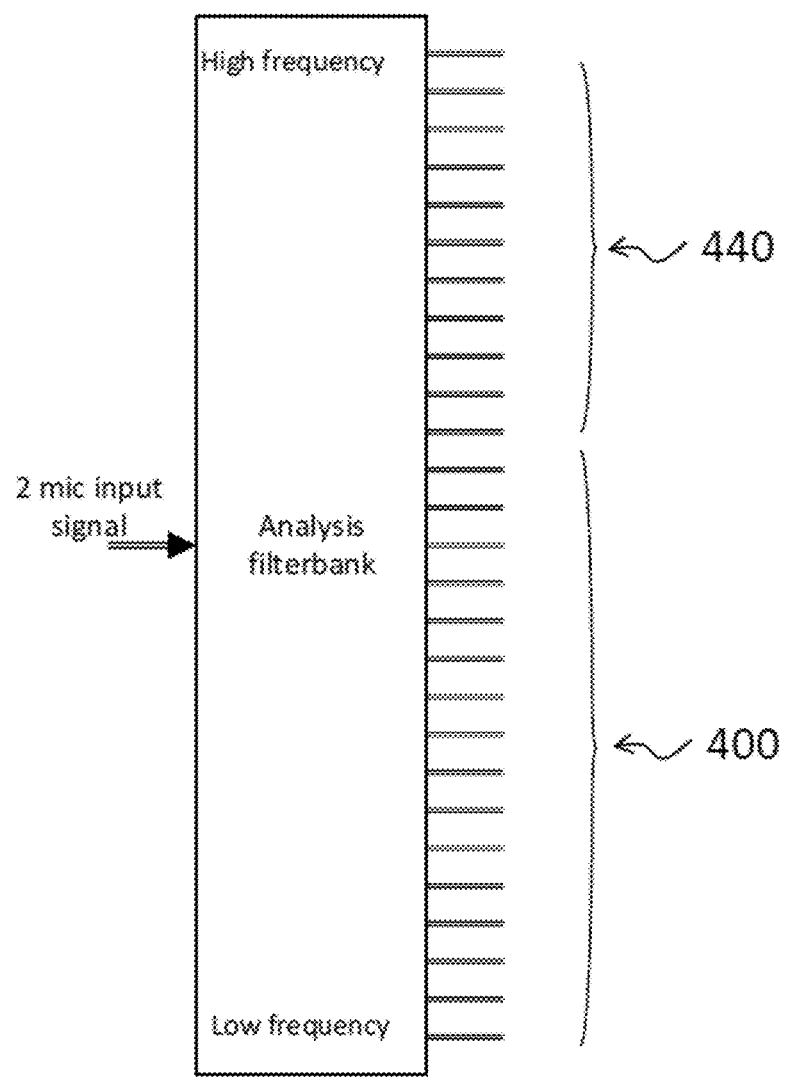
FIG. 8: exemplary depicts a prioritization of the processing of frequency bands to be processed either towards cancelling noise and improving speech intelligibility or towards cancelling feedback.

FIG. 8 shows a prioritization scheme for prioritizing the processing of frequency bands either towards cancelling noise and improving speech intelligibility or towards cancelling feedback. A first and a second acoustic signal received by a first and a second microphone are converted to a first and second (e.g. digitized) time-domain input signal, respectively, and delivered to an analysis filter bank.

In general, the directional processing in different frequency bands could be prioritized either towards cancelling noise and improving speech intelligibility or be prioritized towards cancelling feedback in frequency regions, where only a little speech intelligibility improvement is achieved. Such a prioritization could be based on the measured feedback path and the speech intelligibility band importance index. In order to minimize the power consumption, the bundling of frequency bands can be optimized for as few processing channels as necessary to maintain a sufficient frequency resolution for providing the information contained in the signal in an adequate manner.

In the low and medium frequencies (indicated by curly bracket) 400, directional processing used for noise reduction improves speech intelligibility significantly. Also, at the low frequency regions which are typically below 1000 Hz, feedback is not likely to occur. In the higher frequency region (indicated by curly bracket) 440, which contributes only a little to the overall speech intelligibility, it can be reasonable to prioritize the directional processing from those frequency regions to cancel the feedback path.

In a binaural hearing aid system, the bundling scheme may be the same for both left and right hearing aid. As a consequence, the bundling scheme depends on the feedback path measures at both hearing aids. In another example, the bundling scheme may be different in the left and the right hearing aid. In a yet another example, the bundling scheme is partly the same at left and the right hearing aid, e.g. the bundling scheme may be the same within a frequency range and different within another frequency range.

The prioritization scheme as described above can also be implemented in a hearing aid implant such as a cochlear implant. Then the prioritization of frequency bands could be used and applied to the distribution of electric pulses to a number of said electrodes.

Figures 9, 10:
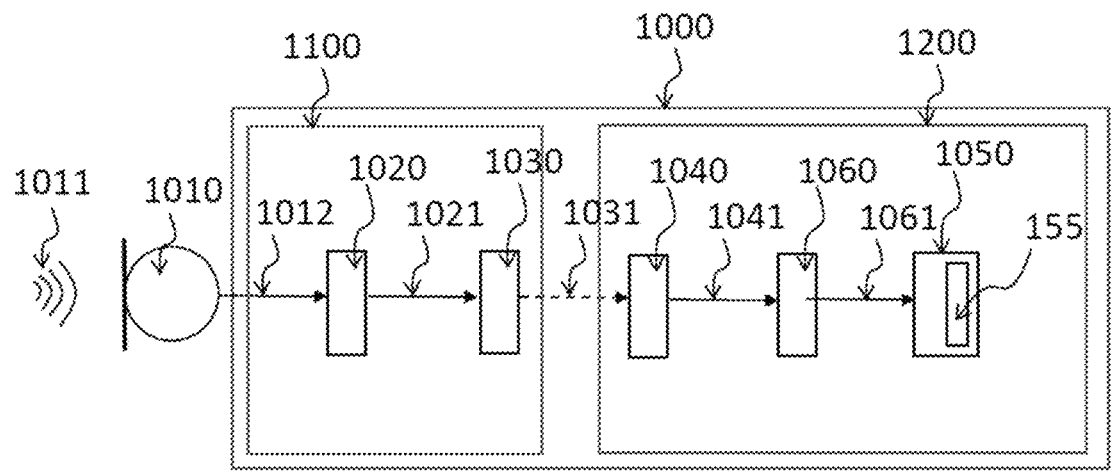
FIG. 9: shows a sketch of a cochlear implant.
FIG. 10: illustrates a bundling of two matrixes.

FIG. 9 shows a cochlear implant 1000 that comprises an external part 1100 and an implanted part 1200. The external part (1100, 1010) comprises at least one input transducer 1010 for capturing incoming sound 1011 and for generating electric audio signals 1012 which represent frequency bands of the incoming sound 1011. A sound processor 1020 is configured to analyze and to process the electric audio signals 1012 and a transmitter 1030 sends the processed electric audio signals 1021 to a receiver/stimulator 1040, e.g. via an inductive link 1031. The receiver/stimulator 1040 receives the processed electric audio signals 1021 from the transmitter 1030 and converts the processed electric audio signals 1021 into electric pulses 1041. A control unit 1060 is configured to control the distribution 1061 of said electric pulses 1041 to the number of said electrodes 1055. An electrode array 1050 which is embedded in (implanted in) cochlea comprises a number of electrodes 155 for stimulating the cochlear nerve with said electric pulses 1041. In the cochlear implant 1000 the distribution of said electric pulses 1041 to the number of said electrodes 155 is performed by applying one out of a plurality of different coding schemes wherein the applied coding scheme is selected according to characteristics of the incoming sound 1011.

FIG. 10 illustrates an example where the bundling and allocation scheme is a two-dimensional matrix comprising ones and zeroes, where ones for example defines a band to be bundled and zeroes defines bands not to be bundled. For example, a column can define the processing channels NP,1 and a row can define input frequency bands NI or vice versa. Thus, the bundling and allocation scheme determines which of the input frequency bands shall be bundled and/or allocated based on a likelihood of feedback to occur the respective input frequency band. The two-dimensional matrix is multiplied by a one-dimensional matrix comprising the number No of output frequency bands. Each of the output frequency bands are identical to the input frequency bands Ni, i.e. No1 is equal to Ni1. The result shows a redistribution of the Np processing channels to a number No of output frequency bands. This allows to filter selected frequency bands that are subject to a high likelihood of feedback or to apply different gain levels to selected frequency bands according to specific hearing situations.

Figure 11:
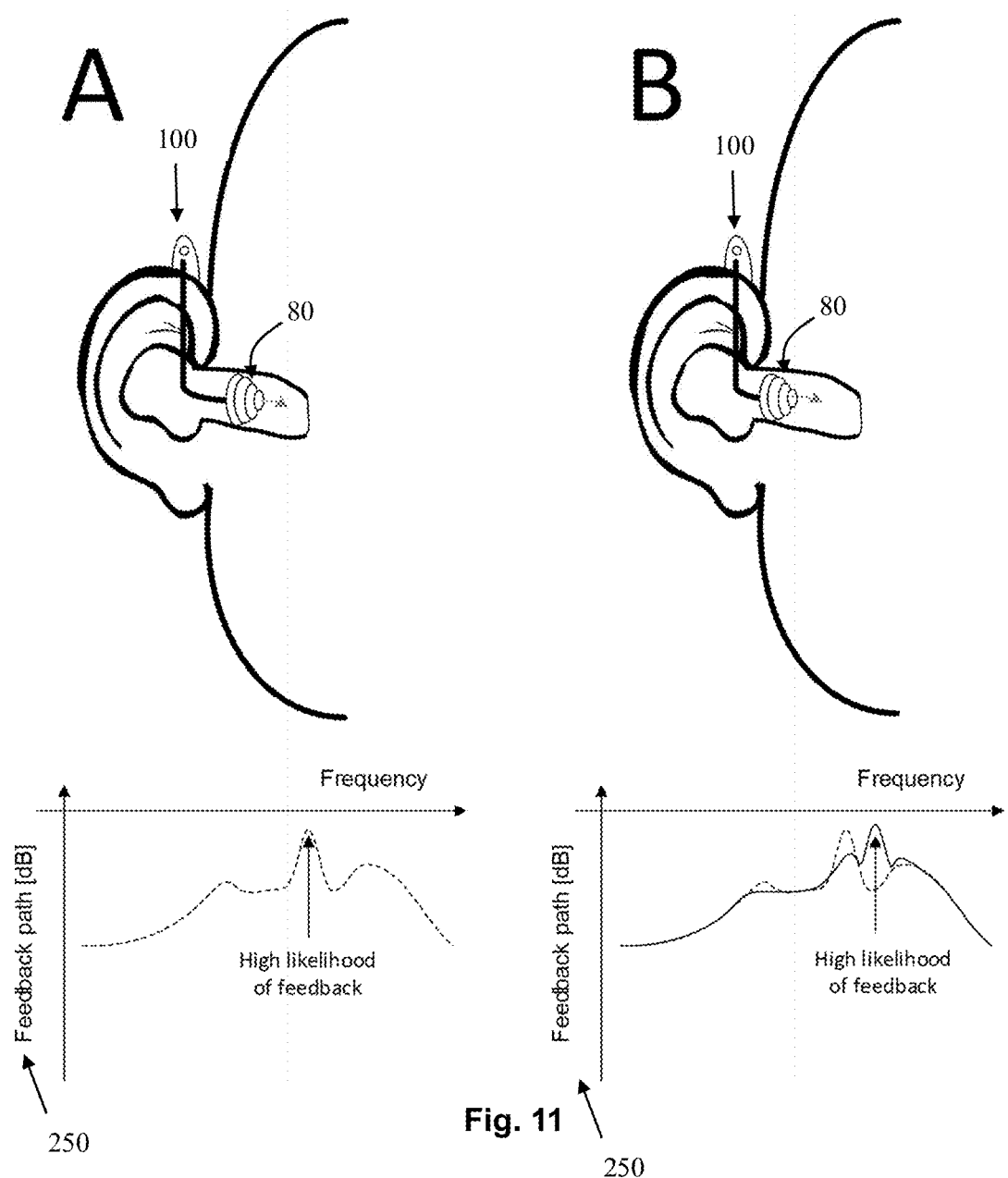
FIG. 11; shows how the feedback path depends on the position of a speaker in an ear of a user, FIG. 12; illustrates how an input signal with a limited bandwidth (such as a telephone signal) can be distributed to bands covering a wider frequency range.

FIG. 11 illustrates different positions of the speaker 80 in an ear of a user of the hearing aid 100 (cf. upper left (A) and right (B) sketches) and the effect on the feedback path 250 as a function of frequency (cf. corresponding lower left and right graphs). It is seen that the peak in the feedback path in dB has shifted upwards in frequency when placing the speaker 80 more outwardly within the ear (right scenario B). In general, the feedback path changes according to the position of the speaker 80 in the ear of a user and hereby different frequency ranges with a high likelihood of feedback are to be expected. Hence, preferably, the frequency band bundling, e.g. the first and/or the second frequency band bundling, may be provided based on a measurement of the feedback path 250 in order to determine whether a change in the feedback path 250 has occurred.

Figure 12:
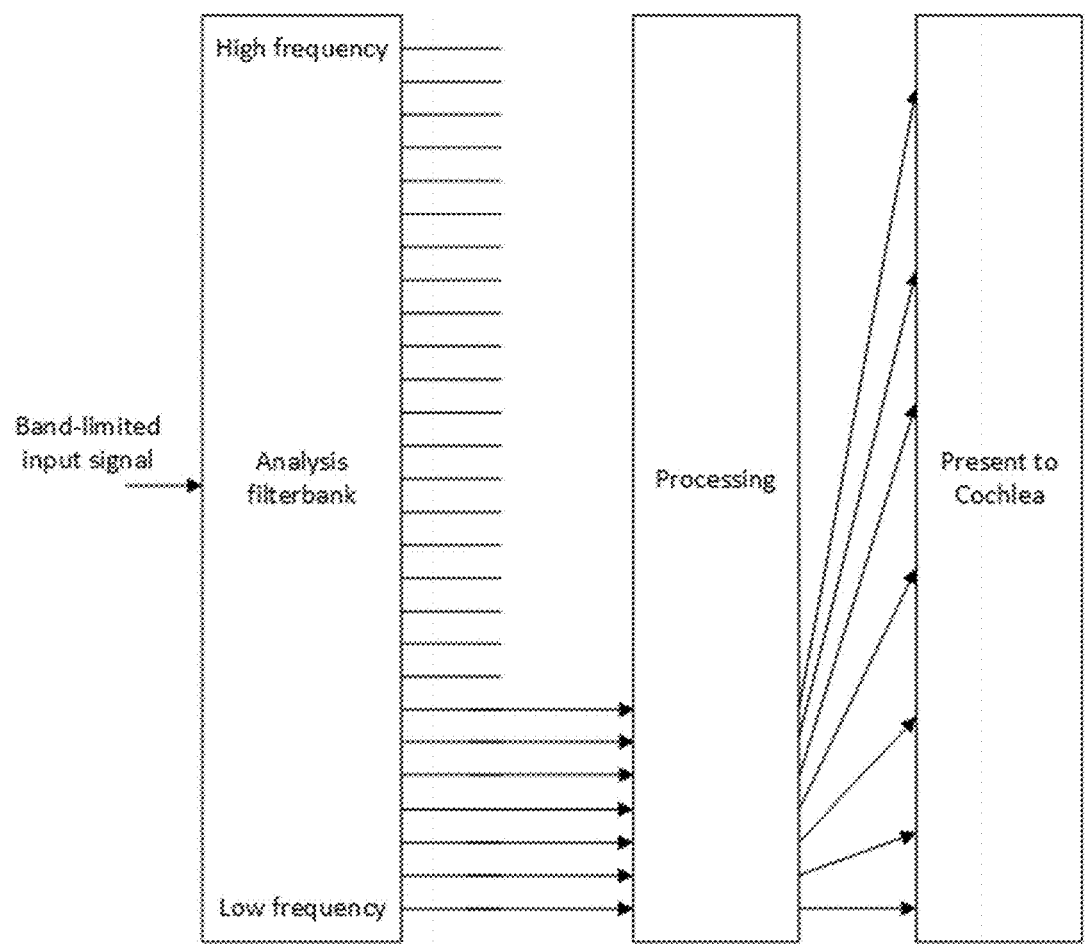

FIG. 12 illustrates how an input signal with a limited bandwidth (such as a telephone signal) can be distributed to bands covering a wider frequency range. This is for example applicable in a cochlear implant, where more information can be transmitted to the brain, if all electrodes are stimulated in contrast to only stimulating electrodes that covers the frequency range of the input stimuli. The re-distribution of a narrow frequency band input signal to a wider output bandwidth can be interpreted as bandwidth extension.

The invention claimed is:

1. A hearing aid device comprising
a first microphone configured to receive a first acoustic signal and to convert the first acoustic signal to a first electrical audio signal,
a speaker configured to emit an acoustic output signal into an ear of a user of the hearing aid device,
a first analog-to-digital converter for converting the first electrical audio signal into a first time-domain input signal,
a first input unit comprising a first analysis filter bank which is configured to convert the first time-domain input signal to a number $N_{I,1}$ of first input frequency bands wherein the number $N_{I,1}$ of first input frequency bands is determined by said first analysis filter bank,
a first frequency band bundling and allocation unit which is configured to bundle adjacent first input frequency bands and to allocate first frequency bands to be processed to a number $N_{P,1}$ of first processing channels,
a memory unit which is configured to store data indicating which of the first $N_{I,1}$ input frequency bands are subject to a likelihood of feedback that is above a predefined threshold,
a signal processing unit which is configured to process the first frequency bands in the number $N_{P,1}$ of first processing channels, and wherein the number $N_{P,1}$ of first processing channels is smaller than the number $N_{I,1}$ of first input frequency bands, and
wherein the first frequency band bundling and allocation unit is configured to generate a first bundling and allocation scheme which determines the bundling of the first $N_{I,1}$ input frequency bands and the allocation of the first frequency bands to be processed to the first $N_{P,1}$ processing channels, wherein said first bundling and allocation scheme depends on the likelihood of feedback to occur in at least one of the first $N_{I,1}$ input frequency bands so as to maintain a higher frequency resolution in the first $N_{P,1}$ processing channels for a frequency region in the first $N_{I,1}$ input frequency bands having a higher likelihood of feedback occurrence than another frequency region having a lower likelihood of feedback occurrence.

2. A hearing aid device according to claim 1, further comprising a first frequency band redistribution unit that is configured to redistribute the $N_{P,1}$ processing channels to a number $N_{O,1}$ of first output frequency bands.

3. A hearing aid device according to claim 2, wherein the signal processing unit is configured to determine a first filter coefficient for each of the $N_{I,1}$ input frequency bands based on the first bundling and allocation scheme, and wherein the acoustic output signal comprises a summation of the filter coefficients each multiplied by the respective of the $N_{O,1}$ first output frequency bands.

4. A hearing aid device according to claim 1 wherein if the likelihood of feedback is above the predefined threshold the respective input frequency band is not bundled within the $N_{P,1}$ processing channels, and if the likelihood of feedback is below the predefined threshold the respective input frequency band is bundled within the $N_{P,1}$ processing channels.

5. A hearing aid device according to claim 1, comprising
a second microphone configured to receive a second acoustic signal and to convert the second acoustic signal to a second electrical audio signal,
a second analog-to-digital converter for converting the second electrical audio signal into a second time-domain input signal,
a second input unit comprising a second analysis filter bank which is configured to convert the second time-domain input signal to a number $N_{I,2}$ of second input frequency bands wherein the number $N_{I,2}$ of second input frequency bands is determined by said second analysis filter bank,
a second frequency band bundling and allocation unit which is configured to bundle adjacent second input frequency bands and to allocate second frequency bands to be processed to a number $N_{P,2}$ of second processing channels,
wherein the memory unit is configured to store data indicating which of the second $N_{I,2}$ input frequency bands is subject to a likelihood of feedback that is above the predefined threshold, and
wherein the signal processing unit is adapted to process the second input frequency bands in the number $N_{P,2}$ of second processing channels, and where the number $N_{P,2}$ of second processing channels is smaller than the number $N_{I,2}$ of second input frequency bands, and
wherein the second frequency band bundling and allocation unit is configured to generate a second bundling and allocation scheme which determines the bundling of the second $N_{I,2}$ input frequency bands and the allocation of the second frequency bands to be processed to the second $N_{P,2}$ processing channels based on the likelihood of feedback to occur in at least one of the second $N_{I,2}$ input frequency bands.

6. A hearing aid device according to claim 5, further comprising a second frequency band redistribution unit that is configured to redistribute the $N_{P,2}$ processing channels to a number $N_{O,2}$ of second output frequency bands.

7. A hearing aid device according to claim 6, wherein the signal processing unit is configured to determine a second set of filter coefficients for each of the second $N_{I,2}$ input frequency bands based on the second bundling and allocation scheme, and wherein the first filter coefficients of the first set of filter coefficients and the second filter coefficients of the second set of filter coefficients comprise a real part and an imaginary part, wherein the imaginary part of the first and second filter coefficients is determined such that the likelihood of feedback to occur is minimised and such that the impact on the part of the acoustic output signal which does not comprise feedback is minimum, and wherein the acoustic output signal comprises a summation of the respective first filter coefficients each multiplied by the respective of the first $N_{O,1}$ output frequency bands and the second filter coefficients each multiplied by the respective of the second $N_{O,2}$ output frequency bands.

8. A hearing aid device according to claim 6, further comprising:
a first frequency band redistribution unit that is configured to redistribute the $N_{P,1}$ processing channels to a number $N_{O,1}$ of first output frequency bands; and
a beamformer filtering unit for providing a beamformed signal based on said first and second output frequency bands.

9. A hearing aid device according to claim 1, wherein the likelihood of feedback is determined by a feedback detection unit which is comprised in the hearing aid device or which is comprised by an external device.

10. A hearing aid device according to claim 9, wherein the feedback detection unit is configured to dynamically determine the likelihood of feedback to occur in at least one of the first $N_{I,1}$ input frequency bands and/or in at least one of the second $N_{I,2}$ input frequency bands, and wherein the first frequency band bundling and allocation unit and/or the second frequency band bundling and allocation unit is/are configured to dynamically control the bundling and allocation of the first $N_{I,1}$ input frequency bands and/or of the $N_{I,2}$ second input frequency bands, respectively.

11. A hearing aid device according to claim 9, wherein the feedback detection unit is configured to adaptively track feedback path changes over time based on a linear time invariant filter which are adapted to estimate the first and/or the second feedback path wherein first and/or the second filter coefficients are updated over time.

12. A hearing aid device according to claim 1, wherein the frequency band bundling and allocation unit is configured to dynamically adapt the number $N_{P,1}$ of first processing channels and/or the number $N_{P,2}$ of second processing channels during normal use of the hearing aid device.

13. A hearing aid device according to claim 1, wherein the signal processing unit is further configured to process speech intelligibility information, and wherein the signal processing unit is further configured to prioritize the processing of the first and/or second frequency bands to be processed either towards cancelling noise and improving speech intelligibility or towards cancelling feedback in frequency bands where only little speech intelligibility improvement is expected.

14. A hearing aid device according to claim 13, wherein the signal processing unit is further configured to prioritize the processing of the frequency bands based on the measured first and/or second feedback path(s) and a speech intelligibility index.

15. A hearing aid device according to claim 1, wherein said hearing aid device is a hearing instrument, a hearing aid, a bone conduction hearing aid, a headset, an earphone, an ear protection device, an active ear protection system, or a combination thereof.

16. A hearing aid device system comprising two or more hearing aid devices according to claim 1, wherein the hearing aid devices are adapted for exchanging information about the bundling of input frequency bands, preferably via a wireless communication link.

17. A hearing aid device system according to claim 16, said hearing aid device system being configured to provide that the same bundling scheme is applied in both hearing aid devices of a binaural system by exchanging synchronizing control signals between the two hearing aid devices.

18. A method of processing an input audio signal comprising
receiving a first acoustic signal and converting the first acoustic signal to a first electrical audio signal
converting the first electrical audio signal into a first time-domain input signal,
converting the first time-domain input signal to a number $N_{I,1}$ of first input frequency bands wherein the number $N_{I,1}$ of first input frequency bands is determined by an analysis filter bank,
bundling of adjacent first input frequency bands and allocating first frequency bands to be processed to a number $N_{P,1}$ of first processing channels,
storing data indicating which of the first $N_{I,1}$ input frequency bands are subject to a likelihood of feedback that is above a threshold,
generating a first bundling and allocation scheme which determines the bundling of the input frequency bands and the allocation of the first frequency bands to be processed to the first $N_{P,1}$ processing channels wherein said first bundling and allocation scheme depends on the likelihood of feedback to occur in at least one of the $N_{I,1}$ input frequency bands so as to maintain a higher frequency resolution in the first $N_{P,1}$ processing channels for a frequency region in the first NIA input frequency bands having a higher likelihood of feedback occurrence than another frequency region having a lower likelihood of feedback occurrence,
processing the first frequency bands to be processed in the number $N_{P,1}$ of first processing channels, wherein the number $N_{P,1}$ of first processing channels is smaller than the number $N_{I,1}$ of first input frequency bands,
determining first filter coefficients for each of the $N_{I,1}$ input frequency bands based on the first bundling and allocation scheme,
redistributing the $N_{P,1}$ processing channels to a number $N_{O,1}$ of first output frequency bands, and
emitting an acoustic output signal into an ear of a user, wherein the acoustic output signal comprises a summation of the first filter coefficients each multiplied by the respective of the $N_{O,1}$ output frequency bands.

19. A method of processing an input audio signal according to claim 18, further comprising
receiving a second acoustic signal and converting the second acoustic signal to a second electrical audio signal
converting the second electrical audio signal into a second time-domain input signal,
converting the second time-domain input signal to a number $N_{I,2}$ of second input frequency bands wherein the number $N_{I,2}$ of second input frequency bands is determined by the analysis filter bank,
bundling of adjacent second input frequency bands and allocating second frequency bands to be processed to a number $N_{P,2}$ of second processing channels,
storing data indicating which of the second $N_{I,2}$ input frequency bands are subject to a likelihood of feedback that is above a threshold,
generating a second bundling and allocation scheme which determines the bundling of the $N_{I,2}$ input frequency bands and the allocation of the second frequency bands to be processed to the second $N_{P,2}$ processing channels wherein said second bundling and allocation scheme depends on the likelihood of feedback to occur in at least one of the $N_{I,2}$ input frequency bands, processing the second frequency bands to be processed in the number $N_{P,2}$ of second processing channels, wherein the number $N_{P,2}$ of second processing channels is smaller than the number $N_{I,2}$ of second input frequency bands, determining second filter coefficients for each of the $N_{I,2}$ input frequency bands based on said second bundling and allocation scheme, redistributing the $N_{P,2}$ processing channels to a number $N_{O,2}$ of second output frequency bands, and emitting an acoustic output signal into an ear of a user, wherein the acoustic output signal comprises a summation of the first filter coefficients each multiplied by the respective of the first $N_{O,1}$ output frequency bands and the second filter coefficients each multiplied by the respective second of the $N_{O,2}$ output frequency bands.

20. A data processing system comprising a processor and program code means adapted to cause the processor to perform the steps of the method of claim 18.

* * * * *